(12) United States Patent
Neurath et al.

(10) Patent No.: US 7,524,851 B2
(45) Date of Patent: Apr. 28, 2009

(54) DIAGNOSTIC METHODS FOR THERAPEUTIC COMPOUNDS AND METHODS FOR MONITORING AZATHIOPRINE THERAPY

(75) Inventors: Markus F. Neurath, Mainz (DE); Matthias Schwab, Stuttgart (DE)

(73) Assignee: Robert Bosch Gesellschaft fur Medizinische Forschung (RBMF), Stuttgart (DE)

( * ) Notice: Subject to any disclaimer, the term of this patent is extended or adjusted under 35 U.S.C. 154(b) by 401 days.

(21) Appl. No.: 11/003,306

(22) Filed: Dec. 2, 2004

(65) Prior Publication Data
US 2005/0220709 A1    Oct. 6, 2005

Related U.S. Application Data

(60) Provisional application No. 60/527,376, filed on Dec. 5, 2003.

(51) Int. Cl.
*A61K 31/52* (2006.01)
*A61K 31/415* (2006.01)

(52) U.S. Cl. .................... 514/262.1; 514/391; 514/395
(58) Field of Classification Search ........................ None
See application file for complete search history.

(56) References Cited

U.S. PATENT DOCUMENTS

| 6,355,623 | B2 | 3/2002 | Seidman et al. |
| 6,680,302 | B2 | 1/2004 | Seidman et al. |

OTHER PUBLICATIONS

Gao et al, 2004 (PNAS. 101(20): 7618-7623).*
Neurath et al, 2005. Clinical Gasteroenterology and Hepatology. 3: 1007-1014.*
Patel et al. 2006. J Am Acad Dermatol. 55(3): 369-89).*
Kenter et al. 2006. Lancet. 368: 1387-1391.*
Brynskov et al. 1990. Gut. 31: 795-799.*
Yuan Gao, et al.; Rational design and characterization of a Rac GTPase-specific small molecule Inhibitor, PNAS; May 18, 2004; vol. 101, No. 20.
Juran Kato-Stankiewicz, et al.; Inhibitors of Ras/Raf-1 interaction identified by two-hybrid screening revert Ras-dependent transformation phenotypes in human cancer cells; PNAS; Oct. 29, 2002; vol. 99, No. 22.
Imke Tiede, et al.; CD28-dependent Rac1 activation is the molecular target of azathioprine in primary human CD4+ T lymphocytes; The Journal of Clinical Investigation; Apr. 2003; vol. III, No. 8.
Dubinsky, Marla C. et al., 6-MP Metabolite Profiles Provide a Biochemical Explanation for 6-MP Resistance in Patients with Inflammatory Bowel Disease; Gastroenterology; vol. 122, No. 4, Apr. 2002, pp. 904-915.
Cuffari C., et al.; Utilisation of erythrocyte 6-thioguanine metabolite levels to optimise azathioprine therapy in patients with inflammatory bowel disease; GUT, vol. 48, No. 5., May 2001, pp. 642-646.
Tiede, I., et al.; CD28-dependent Rac1 activation is the molecular target of azathioprine in primary human CD4+ T lymphocytes; Journal of Clinical Investigation, vol. III, No. 8, Apr. 2003; pp. 1133-1145.

* cited by examiner

*Primary Examiner*—Elizabeth C. Kemmerer
*Assistant Examiner*—Zachary C Howard
(74) *Attorney, Agent, or Firm*—Townsend and Townsend and Crew LLP

(57) ABSTRACT

The present invention provides diagnostic methods for predicting therapeutic efficacy in an individual being treated for an autoimmune or an inflammatory disease. In addition, the present invention also provides novel methods for monitoring azathioprine therapy or optimizing clinical responsiveness to azathioprine therapy in an individual by measuring 6-thioguanosine nucleotide levels in a sample from the individual.

32 Claims, 12 Drawing Sheets

SEQUENCE LISTING

```
<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
      electrophoretic mobility shift assay (EMSA) oligonucleotide
      NF-kappaB

<400> SEQUENCE: 1
agttgagggg actttcccag gc                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      electrophoretic mobility shift assay (EMSA) oligonucleotide
      NF-kappaB
```

-continued

```
<400> SEQUENCE: 2
gcctgggaaa gtcccctcaa ct                                                  22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      electrophoretic mobility shift assay (EMSA) oligonucleotide SP-1

<400> SEQUENCE: 3
attcgatcgg ggcggggcga gc                                                  22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      electrophoretic mobility shift assay (EMSA) oligonucleotide SP-1

<400> SEQUENCE: 4
gctcgccccg ccccgatcga at                                                  22

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:(His)-6 tag

<400> SEQUENCE: 5

His His His His His His
 1               5
```

DIAGNOSTIC METHODS FOR THERAPEUTIC COMPOUNDS AND METHODS FOR MONITORING AZATHIOPRINE THERAPY

CROSS-REFERENCE TO RELATED APPLICATIONS

The present application claims priority to U.S. Provisional Patent Application No. 60/527,376, filed Dec. 5, 2003, the disclosure of which is hereby incorporated by reference in its entirety for all purposes.

BACKGROUND OF THE INVENTION

Immune-mediated gastrointestinal disorders encompass a wide range of debilitating gastrointestinal diseases of various etiologies. One such immune-mediated gastrointestinal disorder, inflammatory bowel disease (IBD), is the collective term used to describe two gastrointestinal disorders of unknown etiology: Crohn's disease (CD) and ulcerative colitis (UC). The course and prognosis of IBD, which occurs world-wide and afflicts millions of people, varies widely. Onset of IBD occurs predominantly in young adulthood, with diarrhea, abdominal pain, and fever being the three most common presenting symptoms. The diarrhea may range from mild to severe and in ulcerative colitis often is accompanied by bleeding. Anemia and weight loss are additional common signs of IBD. Ten to fifteen percent of all patients with IBD will require surgery over a ten year period. In addition, patients with IBD are at increased risk for the development of intestinal cancer. Symptoms such as an increased occurrence of psychological problems, including anxiety and depression, are perhaps not surprising given that IBD is often a debilitating disease that strikes people in the prime of life.

Crohn's disease (CD) is a major form of IBD leading to a chronic granulomatous inflammation that can occur anywhere in the alimentary tract (Podolsky, *N. Engl. J. Med.* 325:928-937 (1991)). Although the precise pathogenesis is still unknown, recent data suggest that genetic factors (e.g., NOD2 mutations), environmental factors (e.g., bacterial antigens), and an activation of the mucosal immune system play a major pathogenic role (Podolsky, supra; Beutler, *Immunity*, 15:5-14 (2001); Neurath et al., *Nat. Med.* 8:567-573 (2002); MacDonald et al., *Scand. J. Immunol.* 51:2-9 (2000); Shanahan, *Lancet* 359:62-69 (2002); Hugot et al., *Nature* 411:599-603 (2001); Ogura et al., *Nature* 411:603-606 (2001); Targan et al., *N. Engl. J. Med.* 337:1029-1035 (1997); Elson et al., *Gastroenterol.* 109:1344-1367 (1995)). In the chronic phase of this disease, cytokines produced by macrophages and T lymphocytes in the lamina propria have been shown to play a key pathogenic role (Atreya et al., *Nat. Med.* 6:583-588 (2000); Breese et al., *Immunology* 78:127-131 (1993); Plevy et al., *J. Immunol.* 159:6276-6282 (1997)). In particular, it has recently been demonstrated that proinflammatory cytokines such as IL-6 and IL-12 may cause T cell resistance against apoptosis in CD that leads to inappropriate lymphocyte accumulation in the gut and disease perpetuation (Atreya et al., supra; Boirivant et al., *Gastroenterol.* 116:557-565 (1999)).

The azathioprine molecule is composed of two moieties: mercaptopurine and an imidazole derivative (Lennard, *Eur. J. Clin. Pharmacol.* 43:329-335 (1992); Hoffmann et al., *J. Am. Chem. Soc.* 123:6404-6409 (2001)). After oral administration and absorption, the pro-drug azathioprine undergoes approximately 90% conversion to 6-MP by non-enzymatic attack by sulfhydryl-containing compounds such as glutathione or cysteine that are present in every mammalian cell (Lennard, supra; Kroplin et al., *Eur. J. Clin. Pharmacol.* 56:343-345 (2000)). 6-MP is then enzymatically converted by xanthine oxidase to 6-thiouric acid, by thiopurine S-methyltransferase (TPMT) to 6-methyl-MP (6-MMP), and by hypoxanthine phosphoribosyl transferase (HPRT) to 6-thioguanine (6-TG). Whereas the TPMT pathway appears to be important for azathioprine-mediated side effects such as myelosuppression, the 6-TG generated by the HPRT pathway most likely mediates the immunosuppressive properties of 6-MP (Lennard, supra). In particular, lymphocytes have been shown to enzymatically convert 6-MP to 6-TG (Van Os et al., *Gut* 39:63-68 (1996)).

Azathioprine and its metabolite 6-mercaptopurine (6-MP) are widely used as immunosuppressive and anti-inflammatory agents in organ transplantation and the treatment of chronic inflammatory diseases as well as in the treatment of leukemia. For instance, azathioprine has been therapeutically used in kidney (McGeown et al., *Lancet* 1:983-991 (1988)) and heart (Andreone et al., *J. Heart Transplant.* 5:13-19 (1986)) transplantation and various autoimmune and chronic inflammatory diseases, such as multiple sclerosis (*Lancet* 2:179 183 (1988)), rheumatoid arthritis (DeSilva et al., *Ann. Rheum. Dis.* 40:560-568 (1981)), systemic lupus erythematosus (Ginzler et al., *Arthritis Rheum.* 18:27-35 (1975)), primary biliary cirrhosis (Christensen et al., *Gastroenterol.* 89:1084-1091 (1985)), and IBD (Candy et al., *Gut* 37:674-678 (1995); Bouhnik et al., *Lancet* 347:215-219 (1996); D'Haens et al., *Gastroenterol.* 112:1475-1481 (1997); Lewis et al., *Gastroenterol.* 118:1018-1024 (2000); Present et al., *N. Engl. J. Med.* 302:981-987 (1980)). Azathioprine is considered the gold standard of immunosuppressive therapy for CD (Present et al., supra; Sandborn et al., *Gastroenterol.* 117: 527-535 (1999)). Interestingly, it has been shown that patients with CD who were treated with azathioprine for only a few weeks did not respond to therapy, suggesting that this drug requires prolonged periods of time to achieve clinical responses (Pearson et al., *Ann. Intern. Med.* 123:132-142 (1995); Ewe et al., (1993) *Gastroenterol.* 105:367-376 (1993)). Furthermore, a recent meta-analysis demonstrated that the odds ratio of response to azathioprine in this disease increased with the cumulative dose administered (Pearson et al., supra).

Although azathioprine has been in clinical use for about four decades (Bean, *Med. J. Aust.* 2:592-593 (1962)), its precise mechanisms of action are still unknown. For example, inhibition of purine nucleotide biosynthesis with suppression of DNA and RNA synthesis and down-regulation of B and T cell function have been suggested as major therapeutic mechanisms of azathioprine (Dimitriu et al., *J. Immunol.* 121:2335-2339 (1978); Lennard, supra; Röllinghoff et al., *Clin. Exp. Immunol.* 15:261-269 (1973); Abdou et al., *Clin. Exp. Immunol.* 13:55-64 (1973); Bach et al., *Clin. Exp. Immunol.* 11:89-98 (1972)). However, it is well accepted that a general inhibition of nucleic acid synthesis is not sufficient to explain the specific effects of azathioprine and 6-MP on the immune system (Elion, *Ann. New York Acad. Sci.* 685:400-407 (1993)). Furthermore, azathioprine and 6-MP require very high dosages to suppress proliferation of primary T cells in vitro that are outside of clinically relevant dosages in IBD patients (Quemeneur et al., *J. Immunol.* 170:4986-4995 (2003)). Taken together, these data make it very likely that another specific mechanism underlies the immunosuppressive properties of azathioprine.

Since unchecked proliferation of lymphocytes may provoke the risk of developing chronic inflammatory or autoimmune diseases such as IBD, the immune system controls efficient elimination of activated lymphocytes in a process known as apoptosis (Scaffidi et al., *Curr. Opin. Immunol.* 11:277-285 (1999); Lenardo et al., *Annu. Rev. Immunol.* 17:221-253 (1999)). This is particularly important for the mucosal immune system, since a resistance of lamina propria cells to apoptosis may lead to chronic inflammatory responses in the gut (Neurath et al., *Trends Immunol.* 22:21-26 (2001)). Thus, there is a need in the art for novel therapeutic methods of inducing the apoptosis of immune cells such as lymphocytes in patients with IBD. There is also a need in the art for novel methods of monitoring, predicting, and/or optimizing clinical responsiveness to therapy in patients with IBD. The present invention satisfies these needs and provides related advantages as well.

BRIEF SUMMARY OF THE INVENTION

The present invention provides diagnostic methods for predicting therapeutic efficacy in an individual being treated for an autoimmune or an inflammatory disease, the method comprising:
(a) providing the individual with a compound that inhibits Rac1 activation to induce apoptosis in a cell; and
(b) determining the concentration of a metabolite of the compound in a sample from the individual to thereby predict therapeutic efficacy.

In another embodiment, the present invention provides methods for monitoring azathioprine therapy or optimizing clinical responsiveness to azathioprine therapy in an individual by measuring at least one 6-thioguanosine nucleotide in a sample from the individual.

In still another aspect, the present invention provides a method for monitoring azathioprine therapy in an individual comprising:
a) measuring the level of 6-thioguanosine diphosphate and 6-thioguanosine triphosphate in a sample from the individual; and
b) calculating a concentration ratio of 6-thioguanosine triphosphate to 6-thioguanosine triphosphate and 6-thioguanosine diphosphate, wherein the ratio is indicative of a characteristic clinical responsiveness to azathioprine therapy in the individual.

In yet another aspect, the present invention provides a method for optimizing clinical responsiveness to azathioprine therapy in an individual comprising:
a) measuring the level of at least one 6-thioguanosine nucleotide in a sample from the individual; and
b) adjusting the subsequent dose of azathioprine or a metabolite thereof based upon the level of the at least one 6-thioguanosine nucleotide.

Other objects, features, and advantages of the present invention will be apparent to one of skill in the art from the following detailed description.

DETAILED DESCRIPTION OF THE INVENTION

I. Abbreviations

Figure 1:
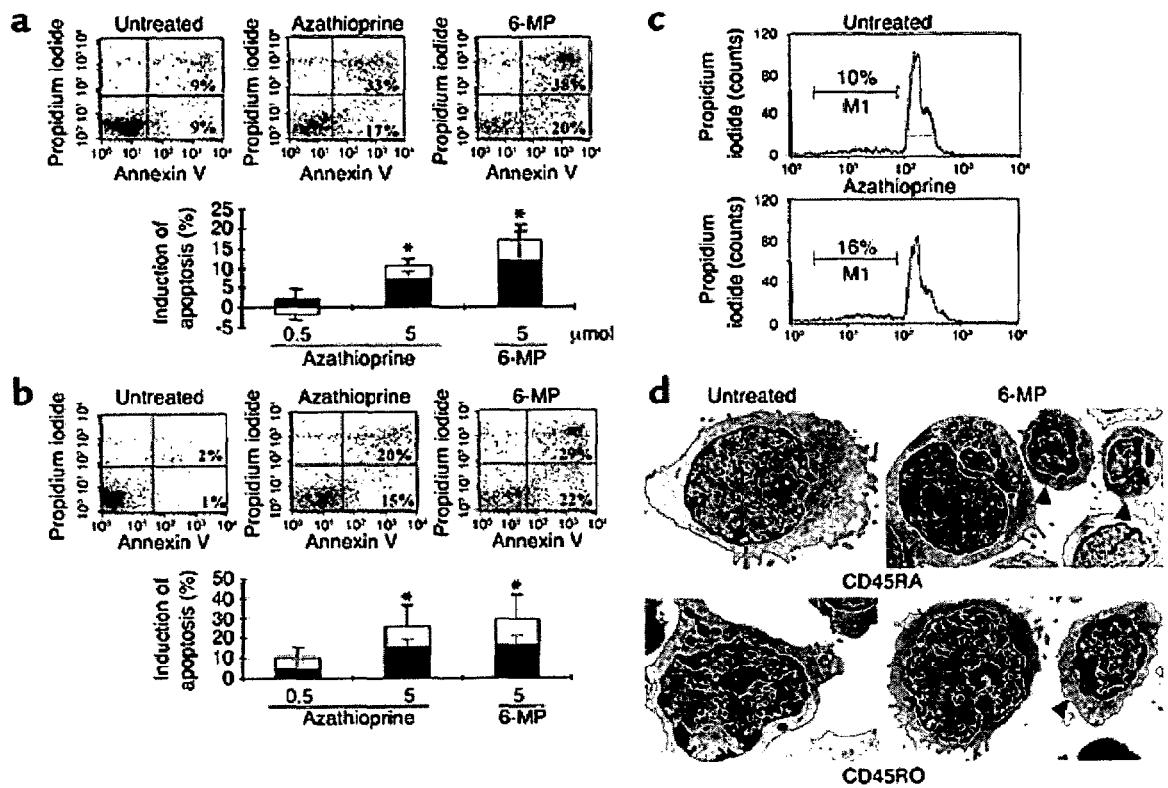
FIG. 1. Azathioprine and its metabolites induce T cell apoptosis. CD45RA (a) and CD45RO (b) T cell subsets were isolated from peripheral blood of healthy volunteers and stimulated with antibodies to CD3 and CD28 and recombinant IL-2 in the presence or absence of indicated concentrations of azathioprine and 6-MP. T cell apoptosis was assessed by FACS analysis after 5 days of cell culture. Azathioprine and 6-MP led to an induction of annexin-positive, propidium iodide-negative T cells, indicating that they induced T cell apoptosis. The FACS data is representative of 6-10 independent experiments per group. The average induction of specific apoptosis from 6-10 patients per group (induction of annexin-positive, propidium iodide-negative cells compared with untreated cells indicated by black sections of bars, induction of annexin-positive, propidium iodide-positive cells compared with untreated cells indicated by white sections) by azathioprine and 6-MP±SEM is shown in the lower panels. Statistically significant changes are indicated (*$P<0.01$). (c) Determination of apoptosis and cell cycle distribution by the Nicoletti technique. Peripheral blood $CD4^+$ T cells from healthy volunteers were stimulated as above for 5 days, followed by analysis of DNA content by the Nicoletti technique. The percentage of apoptotic cells in the subdiploid peak is indicated by M1. (d) Azathioprine and 6-MP induce morphologic changes of CD45RA $CD4^+$ T cells (upper panels) and CD45RO $CD4^+$ T cells (lower panels) indicative of apoptosis, as assessed by transmission electron microscopy. Peripheral blood $CD4^+$ T cells from healthy volunteers were stimulated as above for 5 days. Upon 6-MP treatment, T cells exhibited typical signs of apoptosis (arrowheads), with dense nuclear condensation and degeneration of organelles. Magnification, ×7200.

Azathioprine (AZA); 6-mercaptopurine (6-MP); 6-thioguanine (6-TG); 6-thioguanosine triphosphate (TGTP or 6-Thio-GTP); 6-thioguanosine diphosphate (TGDP); 6-thioguanosine monophosphate (TGMP); inflammatory bowel disease (IBD); Crohn's disease (CD); ulcerative colitis (UC); thiopurine S-methyltransferase (TPMT); hypoxanthine phosphoribosyl transferase (HPRT); red blood cell (RBC); peripheral blood mononuclear cell (PBMC); lamina propria mononuclear cell (LPMC); calcium- and magnesium-free HBSS (HBSS-CMF); T cell receptor (TCR); MAP, mitrogen-activated protein; mitogen-activated protein kinase kinase (MEK); MEK kinase (MEKK); IκB, inhibitor of NF-κB. IKK, IκB kinase; signal transducer and activator of transcription-3 (STAT-3); electrophoretic mobility shift assay (EMSA); mitochondrial membrane potential ($\Delta\Psi_m$); carbonylcyanide-4-(trifluoromethoxy)-phenylhydrazone (FCCP); recombinant IL-2 (rIL-2).

II. Definitions

As used herein, the following terms have the meanings ascribed to them unless specified otherwise.

The term "apoptosis" refers to a type of programmed cell death in which the destruction of a cell occurs from within due to activation of a stimulus or removal of a suppressing agent or stimulus. Generally, apoptosis involves the disintegration of the cell undergoing programmed cell death into membrane-bound particles that are then eliminated by phagocytosis or shedding.

The terms "immune cell," "white blood cell," and "leukocyte" are used interchangeably herein to refer to any cell found with the immune system including, without limitation, granulocytes such as neutrophils, eosinophils, and basophils; lymphocytes such as T cells (e.g., cytotoxic T cells, helper T cells, memory T cells), B cells (e.g., plasma B cells, memory B cells), and natural killer cells; monocytes; macrophages; dendritic cells; splenocytes; mast cells; bone marrow stem cells; and combinations thereof. Preferably, the immune cell is a T cell such as, for example, a CD45RA T cell, a CD45RO memory T cell, a CD4-positive T cell, a preactivated T cell, a lamina propria mononuclear cell, and combinations thereof.

The term "azathioprine or a metabolite thereof" refers to any metabolite of azathioprine that can be used in the methods of the present invention including, without limitation, 6-mercaptopurine (6-MP), 6-thioguanine (6-TG), 6-methyl-mercaptopurine (6-MMP), 6-thiouric acid, 6-methylmercaptopurine riboside (6-MMPR), 6-thioguanosine ribonucleosides, 6-thioguanosine ribonucleotide mono-, di-, and tri-phosphates (e.g., 6-thioguanosine monophosphate (TGMP), 6-thioguanosine diphosphate (TGDP), 6-thioguanosine triphosphate (TGTP)), 6-thioguanosine deoxyribonucleosides, 6-thioguanosine deoxyribonucleotide mono-, di, and tri-phosphates, 6-thioinosine monophosphate, 6-methyl-thioinosine monophosphate, 6-thioxanthosine monophosphate, and derivatives thereof resulting from chemical modifications, so long as the structure of the 6-thioguanosine moiety is preserved.

The term "therapeutically effective amount" as used herein refers to a dose of azathioprine or a metabolite thereof sufficient produce the desired therapeutic effect, e.g., inducing cellular apoptosis, inhibiting Rac1 activation, treating an autoimmune or inflammatory disease, etc., when administered.

The term "autoimmune disease" refers to a disease or disorder resulting from an immune response against a self tissue or tissue component and includes a self antibody response or cell-mediated response. The term autoimmune disease, as used herein, encompasses organ-specific autoimmune diseases in which an autoimmune response is directed against a single tissue and includes inflammatory bowel diseases (IBD) such as Crohn's disease (CD) and ulcerative colitis (UC), Type I diabetes mellitus, myasthenia gravis, vitiligo, Graves' disease, Hashimoto's disease, Addison's disease, autoimmune gastritis, and autoimmune hepatitis. The term autoimmune disease also encompasses non-organ specific autoimmune diseases in which an autoimmune response is directed against a component present in several or many organs throughout the body and includes, for example, rheumatoid disease, systemic lupus erythematosus, progressive systemic sclerosis and variants, polymyositis, and dermatomyositis. Additional autoimmune diseases include, but are not limited to, pernicious anemia, primary biliary cirrhosis, autoimmune thrombocytopenia, Sjögren's syndrome, multiple sclerosis, and psoriasis.

As used herein, the term "immune-mediated gastrointestinal disorder" refers to an autoimmune disease of the gastrointestinal tract or bowel that is mediated by the immune system or cells of the immune system. Immune-mediated gastrointestinal disorders include, without limitation, IBDs such as CD, UC, and indeterminate colitis, lymphocytic colitis, microscopic colitis, collagenous colitis, autoimmune enteropathy, allergic gastrointestinal disease, and eosinophilic gastrointestinal disease.

The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, fibrositis, pelvic inflammatory disease, acne, psoriasis, actinomycosis, dysentery, Lyme disease, heat rash, Stevens-Johnson syndrome, systemic lupus erythematosus, mumps, and blastomycosis.

The term "sample" refers to any biological specimen obtained from an individual. Suitable samples for use in the present invention include, without limitation, whole blood, plasma, serum, red blood cells, saliva, urine, stool (i.e., feces), tears, any other bodily fluid, a tissue sample (e.g., biopsy) such as a small intestine (i.e., duodenum, jejunum, ileum) or colon sample, and cellular extracts thereof (e.g., red blood cellular extract). In a preferred embodiment, the sample is red blood cells. One skilled in the art understands that samples such as red blood cells can be diluted prior to analysis of 6-thioguanosine nucleotide levels.

The term "clinical outcome" refers to any of a variety of symptoms, indexes, factors, markers, etc., useful for determining the effect of azathioprine therapy in an individual in need of such therapy, e.g., having an autoimmune or inflammatory disease, an organ transplant, or leukemia. In some embodiments of the present invention, a characteristic clinical responsiveness to azathioprine therapy is associated with a clinical outcome including, without limitation, an increased or reduced number of flares, an increased or reduced Crohn's disease activity index (CDAI), an increased or reduced colitis activity index (CAI), an increased or reduced demand for steroid treatment, an increased or reduced demand for anti-TNF antibody treatment, increased or reduced CRP levels, and combinations thereof.

The term "administering" as used herein refers to oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

III. General Overview

The present invention is based in part upon the surprising discovery that inhibition of Rac1 activation is mediated by binding of a compound such as 6-thioguanosine triphosphate (TGTP), to Rac1. This binding causes a mitochondrial pathway of T cell apoptosis. The clinical relevance of these findings is underscored by the observation that azathioprine-induced immunosuppression correlates with the presence of apoptotic T cells in the lamina propria of patients with inflammatory bowel disease, whereas patients refractory to azathioprine therapy show no such T cell apoptosis. The present invention is also based upon the surprising discovery that TGTP concentration ratios are indicative of a characteristic clinical responsiveness to azathioprine therapy. In particular, Example 3 below shows that high TGTP levels and/or high TGTP concentration ratios correlate more closely with superior clinical responses (e.g., better clinical outcomes) to azathioprine therapy than high 6-TGN levels in patients with Crohn's disease (CD). Further, Example 3 shows that CD patients with high TGDP levels and/or low TGTP concentration ratios showed a significantly worse outcome with more flares and a greater demand for anti-TNF treatment, despite having high 6-TGN levels. As such, the present invention provides a novel and unexpected link between azathioprine-induced apoptosis of T cells via TGTP and the determination of TGTP levels in individuals on azathioprine therapy for monitoring therapy or predicting and/or optimizing clinical responsiveness to therapy.

IV. Description of the Embodiments

A. Methods of Identifying Compounds and Metabolites

In one aspect, the present invention provides a diagnostic method for predicting therapeutic efficacy in an individual being treated for an autoimmune or an inflammatory disease. The method comprises a) providing the individual with a compound that inhibits Rac1 activation to induce apoptosis in a cell; and b) determining the concentration of a metabolite of the compound in a sample from the individual to thereby predict therapeutic efficacy. The methods include identifying compounds which induce apoptosis in a cell such as an immune cell, by interacting to reduce or inhibit Rac1 activation. The compounds so identified, which are for example useful for the treatment of autoimmune or inflammatory diseases in an individual, can then be provided for therapy. The concentration of metabolite(s) of the identified compound are then determined in a sample from the individual to predict therapeutic efficacy.

The present invention also provides a method for screening for compounds that will be useful for treating autoimmune or inflammatory diseases, comprising either the step of determining whether the compound interacts directly with Rac 1, or the step of determining whether the compound activates Rac1.

Suitable cells (e.g. immune cells) for inducing apoptosis according to the methods of the present invention include, without limitation, granulocytes such as neutrophils, eosinophils, and basophils; lymphocytes such as T cells, B cells, and natural killer cells; monocytes; macrophages; dendritic cells; splenocytes; mast cells; bone marrow stem cells; and combinations thereof. Preferably, the immune cell is a T cell such as, for example, a CD45RA T cell, a CD45RO memory T cell, a CD4-positive T cell, a preactivated T cell, a lamina propria mononuclear cell, and combinations thereof.

In some embodiments, cellular apoptosis is induced upon co-stimulation of the cell with a member selected from the group consisting of interleukin-2, an anti-CD28 antibody, an anti-CD3 antibody, an anti-CD2 antibody, and combinations thereof. In certain instances, cellular apoptosis is induced upon co-stimulation of the cell with interleukin-2, an anti-CD28 antibody, and an anti-CD3 antibody. In certain other instances, cellular apoptosis is induced upon co-stimulation of the cell with interleukin-2, an anti-CD28 antibody, and an anti-CD2 antibody.

Figure 8:
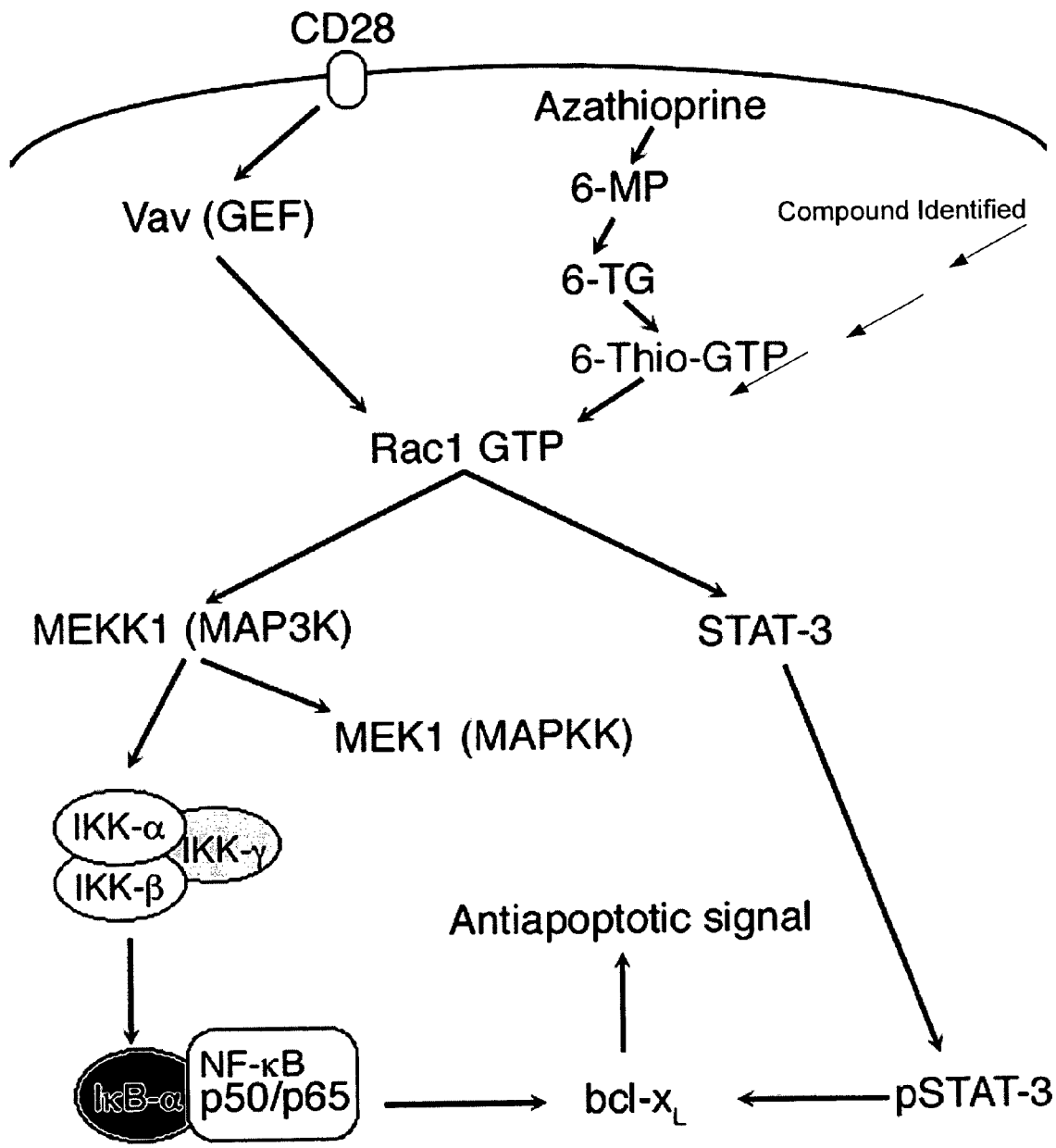
FIG. 8. A model for azathioprine-mediated immunosuppression. Hypothetical mechanism of the action of azathioprine in primary CD4$^+$ T cells upon CD28 costimulation. In normal T cells, CD28 costimulation leads to vav activation, causing replacement of the Rac1-bound GDP with GTP (Kaga et al., *J. Immunol.* 160:4182-4189 (1998)). Activated Rac1 in turn leads to activation of the MEKK/IκB/NF-κB pathway and STAT-3 activation, both of which result in enhanced bcl-x$_L$ levels. Augmented bcl-x$_L$ levels then provide an important antiapoptotic signal. Azathioprine and its metabolites 6-MP and 6-TG specifically target Rac1 activation by the generation of 6-Thio-GTP, which binds to Rac1. Blockade of Rac1 activation leads to suppression of bcl-x$_L$ expression through inhibition of STAT-3 and NF-κB activation, followed by a mitochondrial pathway of apoptosis. MAP, mitrogen-activated protein; IκB, inhibitor of NF-κB. IKK, IκB kinase; MAPKK; MAPK kinase; MAP3K, MAPKK kinase.

As is shown in FIG. 8, in normal T cells, CD28 costimulation leads to vav activation, causing replacement of the Rac1-bound GDP with GTP (Kaga et al., *J. Immunol.* 160: 4182-4189 (1998)). Activated Rac1 in turn leads to activation of the MEKK/IκB/NF-κB pathway and STAT-3 activation, both of which result in enhanced bcl-$x_L$ levels. Augmented bcl-$x_L$ levels then provide an important antiapoptotic signal. In some embodiments, a compound identified using the methods of the present invention specifically targets Rac1 activation by the generation of a metabolite such as 6-Thio-GTP or a derivative thereof, which binds to Rac1. Blockade of Rac1 activation leads to suppression of bcl-x, expression through inhibition of STAT-3 and NF-κB activation, followed by a mitochondrial pathway of apoptosis.

In other embodiments of the present invention, administration to an individual of the identified compound inhibits, e.g., bcl-$x_L$ mRNA and protein expression, NF-κB p50/p65 activation, IκB phosphorylation, MEK phosphorylation, Rac1 activation, or combinations thereof. In a particularly preferred embodiment, administration of the identified compound inhibits Rac1 activation. Preferably, Rac1 inhibition is mediated by the binding of the compound or a metabolite thereof to Rac1. In a preferred aspect, the identified compound or its metabolite has a higher affinity to bind to Rac1 than does 6-thio-GTP.

In another aspect, the present invention provides a method for inhibiting Rac1 activation in a cell comprising administering to the cell an effective amount of azathioprine or a metabolite thereof.

In one embodiment, the cell is an immune cell. Suitable immune cells for inhibiting Rac1 activation according to the methods of the present invention include, without limitation, immune cells such as those described above. Preferably, the immune cell is a T cell such as, for example, a CD45RA T cell, a CD45RO memory T cell, a CD4-positive T cell, a preactivated T cell, a lamina propria mononuclear cell, and combinations thereof.

In another embodiment, a metabolite of the compound so identified is determined. The metabolite can be for example, 6-mercaptopurine (6-MP), 6-thioguanine (6-TG), 6-thioguanosine monophosphate (TGMP), 6-thioguanosine diphosphate (TGDP), 6-thioguanosine triphosphate (TGTP), and derivatives thereof.

In one embodiment, the immune cells for inducing cellular apoptosis include, without limitation, immune cells such as those described above. Preferably, the immune cells are T cells such as, for example, CD45RA T cells, CD45RO memory T cells, CD4-positive T cells, preactivated T cells, lamina propria mononuclear cells, and combinations thereof.

In another embodiment, the autoimmune or inflammatory disease is selected from the group consisting of an immune-mediated gastrointestinal disorder such as inflammatory bowel disease (IBD), rheumatoid arthritis, multiple sclerosis, systemic lupus erythematosus, and primary biliary cirrhosis. Preferably, the methods of the present invention are useful for treating IBDs such as Crohn's disease (CD) and ulcerative colitis (UC). However, one skilled in the art appreciates that any disease or disorder associated with an increase in the activity and/or proliferation of immune cells such as T cells can be treated according to the methods of the present invention.

B. Compounds

As discussed in detail below, blockade of Rac1 activation in a cell is mediated by the binding of a metabolite of an identified compound (e.g., NSC23766, azathioprine, and the like) to Rac1. In operation, blockade of Rac1 target genes causes a mitochondrial pathway of T cell apoptosis. The clinical relevance of these findings is underscored by the observation that azathioprine-induced immunosuppression correlated with the presence of apoptotic T cells in the lamina propria of IBD patients, whereas patients refractory to azathioprine therapy showed no such T cell apoptosis.

In a preferred aspect, the metabolite(s) of compounds of the present invention suppress Rac1 activation in T cells by direct binding to Rac1. Without being bound by any particularly theory, it is believed that the compounds and their metabolite(s), which induce suppression of Rac1, lead to suppression of bcl-$x_L$ expression (through blockade of NF-κB and STAT-3 activation) and thus a mitochondrial pathway of T cell apoptosis. The compounds of the present invention also induce immunosuppression mediated by suppression of Rac1 activation and the consecutive induction of T cell apoptosis.

In certain aspects, the compounds of the present invention inhibit the Rac1-binding interaction with its guanine nucleotide exchange factor (GEF) in a complex formation assay. For this purpose, GEFs that specifically activate Rac1 such as Trio or Tiam1 can be used to assay their binding activity to Rac1 in the presence of an identified compound of interest (see, Gao et al., *PNAS* 101:7618-7623 (2004)). In preferred embodiments, the complex formation assay is performed using tagged (e.g., (His)$_6$ (SEQ ID NO:5), glutathione S-transferase (GST)) or untagged Trio or Tiam1 incubated with tagged (e.g., (His)$_6$ (SEQ ID NO:5), GST) or untagged Rac1. As a non-limiting example, (His)$_6$ (SEQ ID NO:5)-tagged Trio (e.g., 0.5 μg) can be incubated with GST-tagged Rac1 (e.g., 0.5 μg) in a suitable binding buffer (e.g., 20 mM Tris-HCl (pH 7.6), 100 mM NaCl, 1 mM DTT, 1% BSA, 1% Triton X-100, 1 mM MgCl$_2$) with glutathione agarose beads. The identified compound of interest (e.g., at 1 mM concentration) is then added and the assay is allowed to proceed at a suitable temperature (e.g., 4° C.) for a suitable amount of time (e.g., 30 min). After the beads are washed with binding buffer, the amount of (His)$_6$ (SEQ ID NO:5)-tagged Trio that coprecipitated with GST-tagged Rac1 is detected by Western blotting with an anti-His antibody to determine the inhibitory effect of the compound on the interaction between Rac1 and Trio. Alternatively, the assay can be performed using untagged Trio and GST-tagged Rac1, and the amount of Trio that coprecipitated with GST-tagged Rac1 detected by Western blotting with an anti-Trio antibody. In certain other instances, the assay can be performed by immunoprecipitating a complex of untagged Trio and Rac1 with an anti-Rac1 antibody, and the amount of Trio that coprecipitated with Rac1 detected by Western blotting with an anti-Trio antibody. One skilled in the art will appreciate additional types and combinations of tagged and untagged Trio, Tiam1, and Rac1 proteins suitable for use in the assays of the present invention as well as additional conditions (e.g., protein quantity, binding buffer, incubation temperature or time) suitable for performing the assays of the present invention.

In a preferred embodiment, the compound of the present invention is NCS23766, which has the following structure:

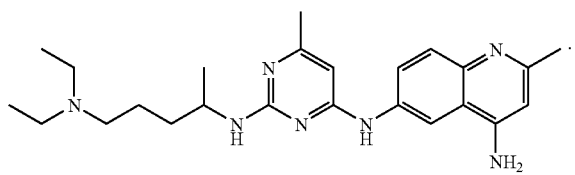

It is believed that the major bonding involved in the interaction between NCS23766 and Rac1 is hydrophobic in nature. The nitrogen atoms of NSC23766 form three hydrogen bonds with residues from the backbone of Rac1, and the stacking effect of the middle pyrimidine ring of NSC23766 with the indole ring of Trp56 may also contribute significantly to the interaction. The interaction between Trp56 and the aromatic ring of NSC23766 may govern the binding specificity, and the side chain of Trp56 in Rac1 provides sufficient bonding for the recognition of NCS23766.

In another aspect, the identified compound of the present invention is azathioprine or 6-mecaptopurine. Azathioprine-induced apoptosis affects mainly CD45RO effector T cells upon costimulation with CD28, indicating that azathioprine can be particularly effective in eliminating pathogenic memory T cells in autoimmune and chronic inflammatory diseases. A therapeutic metabolite of azathioprine is 6-thioguanosine triphosphate (TGTP).

In another aspect, identified compounds of the present invention have metabolites that bind with higher affinity to Rac1 than does 6-TGTP. In certain instances, the compounds which generate such metabolites are more useful in achieving more powerful immunosuppression in autoimmune diseases, inflammatory diseases, and organ transplantation, than azathioprine.

In still certain other aspects, the identified compounds of the present invention are used in combination with inhibitors of Ras/Raf-1 interaction (see, Kato-Stankiewicz et al., *PNAS*, 99:14398-14403 (2002)). Raf is a small GTP-binding protein and is a well studied proto-oncogene. The activation of Ras initiates a complex array of signal transduction events. Specific small molecule inhibitors of Ras/Raf-1 interaction are disclosed in Kato-Stankiewicz et al., *PNAS*, 99, 14398-14403 (2002)), such as MCP1 ($C_{29}H_{27}ClN_2O_3$), MCP53, MCP110 ($C_{33}H_{36}N_2O_3$), and MCP122 ($C_{22}H_{24}N_2O_2$). Other Raf/Ras binding compounds are disclosed in PCT Publication No. WO 03/054193.

C. Metabolites

Preferably, Rac1 inhibition is mediated by the binding of a metabolite of the identified compound to Rac1. The metabolite(s) can be identified by routine organic chemical analysis such as with nuclear magnetic resonance, tandem mass spectrometry, and the like. The metabolite can be, for example, 6-mercaptopurine (6-MP), 6-thioguanine (6-TG), 6-thioguanosine monophosphate (TGMP), 6-thioguanosine diphosphate (TGDP), 6-thioguanosine triphosphate (TGTP), and derivatives thereof. In a preferred aspect, the metabolite has a higher affinity to bind to Rac1 than does TGTP. A particularly efficacious metabolite of NSC23766 has the following structure:

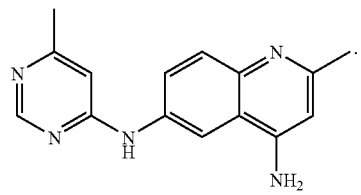

D. Azathioprine Monitoring

In a further aspect, the present invention provides a method for monitoring azathioprine therapy in an individual comprising measuring the level of at least one 6-thioguanosine nucleotide in a sample from the individual.

In one embodiment, the individual has an immune-mediated gastrointestinal disorder such as IBD. In certain instances, the individual has CD. In certain other instances, the individual has UC. In another embodiment, the at least one 6-thioguanosine nucleotide is selected from the group consisting of 6-thioguanosine monophosphate (TGMP), 6-thioguanosine diphosphate (TGDP), 6-thioguanosine triphosphate (TGTP), combinations thereof, and derivatives thereof.

In another embodiment, the level of the at least one 6-thioguanosine nucleotide is indicative of a characteristic clinical responsiveness to azathioprine therapy in the individual. In certain instances, a high 6-thioguanosine triphosphate (TGTP) level is indicative of superior clinical responsiveness to azathioprine therapy. More particularly, a superior clinical responsiveness to azathioprine therapy can be associated with a better clinical outcome such as, for example, a reduced number of flares, a reduced Crohn's disease activity index (CDAI), a reduced colitis activity index (CAI), a reduced demand for steroid treatment, a reduced demand for anti-TNF antibody treatment, reduced C-reactive protein (CRP) levels, and combinations thereof. Preferably, a superior clinical responsiveness to azathioprine therapy is associated with the apoptosis of T cells. In certain other instances, a high 6-thioguanosine diphosphate (TGDP) level is indicative of inferior clinical responsiveness to azathioprine therapy. More particularly, an inferior clinical responsiveness to azathioprine therapy can be associated with a worse clinical outcome such as, for example, an increased number of flares, an increased CDAI, an increased CAI, an increased demand for steroid treatment, an increased demand for anti-TNF antibody treatment, increased CRP levels, and combinations thereof.

In yet another embodiment, the methods of the present invention further comprise calculating a concentration ratio of 6-thioguanosine triphosphate (TGTP) to 6-thioguanosine triphosphate (TGTP) and 6-thioguanosine diphosphate (TGDP), i.e., TGTP/(TGTP+TGDP). In some embodiments, the concentration ratio is indicative of a characteristic clinical responsiveness to azathioprine therapy in the individual. In certain instances, the ratio is indicative of superior clinical responsiveness to azathioprine therapy. For example, as described in Example 3 below, a ratio of greater than about 0.85 is associated with better clinical outcomes and is therefore indicative of superior clinical responsiveness to azathioprine therapy. In certain other instances, the ratio is indicative of inferior clinical responsiveness to azathioprine therapy. For example, as described in Example 3 below, a ratio of less than about 0.85 is associated with worse clinical outcomes and is therefore indicative of inferior clinical responsiveness to azathioprine therapy.

In a further embodiment, the methods of the present invention further comprise calculating a concentration ratio of 6-thioguanosine diphosphate (TGDP) to 6-thioguanosine diphosphate (TGDP) and 6-thioguanosine triphosphate (TGTP), i.e., TGDP/(TGDP+TGTP). In certain instances, the ratio is indicative of superior clinical responsiveness to azathioprine therapy. For example, a low TGDP ratio is typically associated with better clinical outcomes and is therefore indicative of superior clinical responsiveness to azathioprine therapy. In certain other instances, the ratio is indicative of inferior clinical responsiveness to azathioprine therapy. For example, a high TGDP ratio is typically associated with worse clinical outcomes and is therefore indicative of inferior clinical responsiveness to azathioprine therapy.

In some embodiments, the sample used for measuring 6-thioguanosine nucleotide levels includes, without limitation, whole blood, plasma, serum, red blood cells, saliva, urine, stool, tears, any other bodily fluid, a tissue sample such as a small intestine or colon sample, and cellular extracts thereof. Preferably, the sample is blood or red blood cells. In other embodiments, the methods of the present invention further comprise comparing the level of the at least one 6-thioguanosine nucleotide to the level of the same 6-thioguanosine nucleotide measured at an earlier time.

In a preferred embodiment, the present invention provides a method for monitoring azathioprine therapy in an individual comprising:
a) measuring the level of 6-thioguanosine diphosphate and 6-thioguanosine triphosphate in a sample from the individual; and
b) calculating a concentration ratio of 6-thioguanosine triphosphate to 6-thioguanosine triphosphate and 6-thioguanosine diphosphate, wherein the ratio is indicative of a characteristic clinical responsiveness to azathioprine therapy in the individual.

In yet another aspect, the present invention provides a method for optimizing clinical responsiveness to azathioprine therapy in an individual comprising:
a) measuring the level of at least one 6-thioguanosine nucleotide in a sample from the individual; and
b) adjusting the subsequent dose of azathioprine or a metabolite thereof based upon the level of the at least one 6-thioguanosine nucleotide.

In one embodiment, the individual has an immune-mediated gastrointestinal disorder such as IBD. In certain instances, the individual has CD. In certain other instances, the individual has UC. In another embodiment, the at least one 6-thioguanosine nucleotide is selected from the group consisting of 6-thioguanosine monophosphate (TGMP), 6-thioguanosine diphosphate (TGDP), 6-thioguanosine triphosphate (TGTP), combinations thereof, and derivatives thereof.

In yet another embodiment, the level of the at least one 6-thioguanosine nucleotide is indicative of a characteristic clinical responsiveness to azathioprine therapy in the individual. In certain instances, a high 6-thioguanosine triphosphate (TGTP) level is indicative of superior clinical responsiveness to azathioprine therapy. In certain other instances, a high 6-thioguanosine diphosphate (TGDP) level is indicative of inferior clinical responsiveness to azathioprine therapy. In these instances, the subsequent dose of azathioprine or a metabolite thereof is increased. One skilled in the art can readily determine an increased dosage of the drug to administer to the individual.

In additional embodiments, the methods of the present invention further comprise calculating a concentration ratio of 6-thioguanosine triphosphate (TGTP) to 6-thioguanosine triphosphate (TGTP) and 6-thioguanosine diphosphate (TGDP), i.e., TGTP/(TGTP+TGDP). In some embodiments, the concentration ratio is indicative of a characteristic clinical responsiveness to azathioprine therapy in the individual. In certain instances, the ratio is indicative of superior clinical responsiveness to azathioprine therapy. For example, as described in Example 3 below, a ratio of greater than about 0.85 is associated with better clinical outcomes and is therefore indicative of superior clinical responsiveness to azathioprine therapy. In certain other instances, the ratio is indicative of inferior clinical responsiveness to azathioprine therapy. For example, as described in Example 3 below, a ratio of less than about 0.85 is associated with worse clinical outcomes and is therefore indicative of inferior clinical responsiveness to azathioprine therapy. In these instances, the subsequent dose of azathioprine or a metabolite thereof is increased.

In some embodiments, the sample used for measuring 6-thioguanosine nucleotide levels includes, without limitation, whole blood, plasma, serum, red blood cells, saliva, urine, stool, tears, any other bodily fluid, a tissue sample such as a small intestine or colon sample, and cellular extracts thereof. Preferably, the sample is blood or red blood cells. In other embodiments, the methods of the present invention further comprise comparing the level of the at least one 6-thioguanosine nucleotide to the level of the same 6-thioguanosine nucleotide measured at an earlier time.

1. Clinical Subtypes of IBD

Crohn's disease (i.e., regional enteritis) is a disease of chronic inflammation that can involve any part of the gastrointestinal tract. Commonly, the distal portion of the small intestine, i.e., the ileum, as well as the cecum are affected. In other cases, the disease is confined to the small intestine, colon, or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of Crohn's disease are abdominal pain, diarrhea, and recurrent fever. Crohn's disease is commonly associated with intestinal obstruction or fistula, an abnormal passage between diseased loops of bowel. Crohn's disease also includes complications such as inflammation of the eye, joints, and skin, liver disease, kidney stones, and amyloidosis. In addition, Crohn's disease is associated with an increased risk of intestinal cancer.

Several features are characteristic of the pathology of Crohn's disease. The inflammation associated with Crohn's disease, known as transmural inflammation, involves all layers of the bowel wall. Thickening and edema, for example, typically also appear throughout the bowel wall, with fibrosis present in long-standing forms of the disease. The inflammation characteristic of Crohn's disease is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of Crohn's disease.

A hallmark of Crohn's disease is the presence of discrete aggregations of inflammatory cells, known as granulomas, which are generally found in the submucosa. Some Crohn's disease cases display typical discrete granulomas, while others show a diffuse granulomatous reaction or a nonspecific transmural inflammation. As a result, the presence of discrete granulomas is indicative of Crohn's disease, although the absence of granulomas also is consistent with the disease. Thus, transmural or discontinuous inflammation, rather than the presence of granulomas, is a preferred diagnostic indicator of Crohn's disease (see, e.g., Rubin and Farber, Pathology (Second Edition) Philadelphia: J.B. Lippincott Company (1994)).

Ulcerative colitis is a disease of the large intestine characterized by chronic diarrhea with cramping, abdominal pain, rectal bleeding, loose discharges of blood, pus, and mucus. The manifestations of ulcerative colitis vary widely. A pattern of exacerbations and remissions typifies the clinical course for about 70% of ulcerative colitis patients, although continuous symptoms without remission are present in some patients with ulcerative colitis. Local and systemic complications of ulcerative colitis include arthritis, eye inflammation such as uveitis, skin ulcers, and liver disease. In addition, ulcerative colitis, and especially the long-standing, extensive form of the disease is associated with an increased risk of colon carcinoma.

Ulcerative colitis is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach, or esophagus. In addition, ulcerative colitis is distinguished by a superficial inflammation of the mucosa that generally spares the deeper layers of the bowel wall. Crypt abscesses, in which degenerated intestinal crypts are filled with neutrophils, are also typical of ulcerative colitis (Rubin and Farber, supra).

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers, or fistulas suggests Crohn's disease.

Indeterminate colitis is a clinical subtype of IBD that includes both features of Crohn's disease and ulcerative colitis. Such an overlap in the symptoms of both diseases can occur temporarily (e.g., in the early stages of the disease) or persistently (e.g., throughout the progression of the disease) in patients with indeterminate colitis. Clinically, indeterminate colitis is characterized by abdominal pain and diarrhea with or without rectal bleeding. For example, colitis with intermittent multiple ulcerations separated by normal mucosa is found in patients with the disease. Histologically, there is a pattern of severe ulceration with transmural inflammation. The rectum is typically free of the disease and the lymphoid inflammatory cells do not show aggregation. Although deep slit-like fissures are observed with foci of myocytolysis, the intervening mucosa is typically minimally congested with the preservation of goblet cells in patients with indeterminate colitis.

V. Examples

The following examples are offered to illustrate, but not to limit, the claimed invention.

Example 1

CD28-dependent Rac1 Activation is the Molecular Target of Azathioprine in Primary Human CD4$^+$ T Lymphocytes This example illustrates that blockade of Rac1 activation is mediated by binding of the azathioprine metabolite 6-thioguanosine triphosphate (TGTP) to Rac1. Consequently, blockade of Rac1 target genes causes a mitochondrial pathway of T cell apoptosis. The clinical relevance of these findings is underscored by the observation that azathioprine-induced immunosuppression correlated with the presence of apoptotic T cells in the lamina propria of IBD patients, whereas patients refractory to azathioprine therapy showed no such T cell apoptosis.

Methods:

Isolation of primary CD4$^+$ T lymphocytes and lamina propria cells: Human peripheral blood mononuclear cells (PBMCs) from healthy volunteers (25-42 years of age) and patients with Crohn's disease (31-65 years of age) were isolated using Ficoll-Hypaque gradients. PBMCs were further purified using CD4 monoclonal antibodies attached to immunomagnetic beads according to the manufacturer's protocol, followed by treatment with Detachabead (Dynal; Oslo, Norway). In some cases, CD4$^+$ T cells were further separated by negative selection techniques using CD45RO or CD45RA monoclonal antibodies (PharMingen; Heidelberg, Germany) and immunomagnetic beads (Dynal). Reanalysis of sorted populations revealed a purity of over 96%. Lamina propria mononuclear cells (LPMCs) from patients with IBD were isolated from gut specimens using a short-term (5-minute) digestion protocol with collagenase V, hyaluronidase (Sigma-Aldrich; St. Louis, Mo., USA), and DNase (Roche; Mannheim, Germany), as recently described in detail in Holtmann et al., *Eur. J. Immunol.* 32:3142-3151 (2002). Briefly, specimens were washed in calcium- and magnesium-free HBSS (HBSS-CMF), cut into 0.5-cm pieces, and incubated twice in HBSS containing EDTA (0.37 mg/ml) and DTT (0.145 mg/ml) at 37° C. for 15 minutes, followed by subsequent digestion for 5 minutes with collagenase V 400 (1 mg/ml), deoxyribonuclease (0.1 mg/ml DNase), and hyaloronidase (0.1 mg/ml) in a shaking incubator at 37° C. The digested tissue was washed twice in RPMI medium containing 10% FCS and centrifuged. The tissue was finally mechanically homogenized (DAKO homogenizer; Hamburg, Germany) for 4 minutes, and cells were filtered through a sterile 40-µm cell strainer (Falcon; San Diego, Calif., USA). The cells were then cultured in the presence or absence of azathioprine, as specified below.

Cell culture and stimulation conditions: Cell cultures of T cells were performed in complete medium consisting of RPMI-1640 (Biochrom KG; Berlin, Germany) supplemented with 3 mM L-glutamine (Whittaker; Walkersville, Md., USA), 100 U/ml each of penicillin and streptomycin (Whittaker), and 10% heat-inactivated FCS (PAA Laboratories; Linz, Austria).

T cell stimulation for the analysis of azathioprine- and 6-MP-induced apoptosis: T lymphocytes were stimulated in cell culture for 3-5 days with coated antibodies to CD3 (0.04 µg/ml HIT3a, PharMingen) and soluble CD28 antibodies (1 µg/ml, PharMingen). Such CD28 costimulation is known to prevent apoptosis of primary T cells during T cell receptor (TCR) stimulation through activation of bcl-x, and NF-κB (Noel et al., *J. Immunol.* 157:636-647 (1996); Radvanyi et al., *J. Immunol.* 156:1788-1798 (1996); Khoshnan et al., *J. Immunol.* 165:1743-1754 (2000)). No further increase in T cell proliferation was observed upon administration of 10- or even 100-fold increased dosages of anti-CD3 antibodies (mean values of three experiments: no anti-CD, 138,667 cpm; 0.004 µg/ml, 296,500 cpm; 0.4 µg/ml, 306,333 cpm; 4 µg/ml, 348,500 cpm), which strongly suggests that the anti-CD3 dosage used is optimal and that there is a true CD28-dependent effect on Rac1 and NF-κB activation. In addition, recombinant IL-2 (R&D Systems; Wiesbaden, Germany) was used at a final concentration of 40 U/ml in all experiments. Lamina propria T lymphocytes were stimulated with antibodies to CD2 (4 µg/ml; Immunotech; Marseille, France) and CD28 (1 µg/ml). Azathioprine, 6-MP, and 6-TG (Sigma-Aldrich) were added to the T cell cultures at indicated concentrations and time points. To block CD95L-mediated (FasL-mediated) apoptosis, the NOK-1 antibody (4 µg/ml, PharMingen) was used whose Fab fragments bind to human CD95L (FasL)

(Jodo et al., *J. Immunol.* 165:5487-5494 (2000)). Recombinant human FasL (Alexis Biochemicals; Heidelberg, Germany) was used as a positive control for the NOK-1 antibody (10 µg/ml).

Analysis of T cell vitality and clonal expansion: To induce T cell expansion, purified T lymphocytes were stimulated with coated antibodies to CD3 (0.04 µg/ml), soluble antibodies to CD28 (1 µg/ml), and recombinant IL-2 (40 U/ml) for the indicated periods of time. Stimulated T lymphocytes were cultured in the presence or absence of azathioprine or 6-MP (Sigma-Aldrich). Cell viability was assessed by trypan blue (Sigma-Aldrich) staining at the beginning and at the end of the cell culture. The clonal expansion of T cells during cell culture was calculated by the ratio between cell numbers at the beginning and at the end of the cell culture.

FACS analysis: Analysis of peripheral blood T cells and lamina propria T lymphocytes by FACS (FACSscan; Becton Dickinson; Berlin, Germany) was performed using FITC-labeled murine antibodies to human CD4 (PharMingen), anti-mouse IgG1 isotype control antibodies (PharMingen), antibodies to bcl-$x_L$ and p mitogen-activated protein kinase kinase (pMEK) (Santa Cruz Biotech; Santa Cruz, Calif., USA), and goat anti-mouse Fab-FITC (DAKO). For intracellular staining analysis, T cells were fixed in PBS/4% paraformaldehyde (Merck; Munich, Germany) for 10 minutes at 4° C., washed twice in PBS, permeabilized in PBS/0.1% Triton X-100 (Sigma-Aldrich; Steinheim, Germany), and treated with mouse anti-human bcl-$x_L$ or MEK antibodies (2 µg per 5×10$^5$ cells) for 30 minutes on ice. T cells were washed twice in PBS/0.1% Triton X-100 before incubation with goat anti-mouse Fab-FITC (2 µl per 10$^5$ cells). Finally, T cells were washed twice in PBS before FACS analysis.

Analysis of cell apoptosis by annexin V staining and by staining according to Nicoletti: To determine induction of apoptosis in primary T lymphocytes, cells were coincubated with the indicated amounts of azathioprine, 6-MP, or 6-TG and then analyzed by FACS. For FACS analysis, apoptotic cells were detected by staining with annexin V and propidium iodide using the Annexin V FITC Apoptosis Detection Kit I (PharMingen) (Atreya et al., *Nat. Med.* 6:583-588 (2000)). In brief, T cells were washed twice in PBS, and the pellet was resuspended in annexin V binding buffer (PharMingen) at a concentration of 10$^6$ cells per milliliter. Annexin V FITC and propidium iodide were added (5 ill of each per 10$^5$ cells). Samples were gently mixed and incubated for 15 minutes at room temperature in the dark before FACS analysis. To verify the results obtained with the annexin V/propidium iodide staining, analysis of T cells displaying DNA fragmentation was also determined by the Nicoletti technique, as described in (Nicoletti et al., *J. Immunol. Methods* 139:271-279 (1991)). 10$^6$ T cells were fixed in 70% ethanol, washed once in HBSS, resuspended in 1 ml of HBSS and 1 ml of phosphate citric acid buffer (0.2 mol/l Na$_2$PO$_4$ and 0.004 mol/l citric acid [pH 7.8]), and incubated at room temperature for 5 minutes. After centrifugation, cells were resuspended in 1 ml of HBSS containing 20 µg/ml propidium iodide and 10 U DNase-free RNase A and incubated at room temperature for 30 minutes. Finally, cells were analyzed on a FACScan flow cytometer. Because of the fragmentation of DNA, apoptotic cells appear as hypodiploid in the DNA histogram.

Analysis of cellular apoptosis by transmission electron microscopy: For transmission electron microscopy, cells were coincubated with 6-MP (5 µM), washed in PBS, and fixed in 2.5% glutaraldehyde (pH 7.2) overnight. Cells were postfixed in 1% osmium tetroxide for 2 hours and dehydrated in graded ethanol. After transfer to propylene oxide, the cells were finally embedded in agar 100 resin (Plano: Wetzlar, Germany) followed by polymerization at 60° C. for 24 hours. Semithin and 80-nm ultrathin sections were made with an ultramicrotome (Ultracut; Reichert-Jung, Vienna, Austria) and placed on grids. Ultrastructural analysis and photomicroscopy were performed with a transmission electron microscope (model EM 410; Philips, Eindhoven, the Netherlands).

Measurement of 6-TG levels in primary CD4$^+$ T lymphocytes: T lymphocytes were stimulated with antibodies to CD3 and to CD28 as described above and treated with the indicated amounts of azathioprine for 5 days. Cells were washed in PBS, and the pellet was lysed in 200 µl of dH$_2$O followed by addition of 200 µL of 2N H$_2$SO$_4$. The samples were boiled at 95° C. for 15 minutes to release 6-TG. Samples were analyzed for 6-TG content using high-performance liquid chromatography, as described in (Kroplin et al., *Eur. J. Clin. Pharmacol.* 56:343-345 (2000)).

Isolation of mRNA from primary T lymphocytes: T lymphocytes were stimulated with antibodies to CD3 and CD28 in the presence or absence of azathioprine or 6-MP. The mRNA of T cells was extracted at the indicated time points using the Tri-reagent (Sigma-Aldrich) according to the manufacturer's protocol. In brief, the cell pellet was lysed in 1 ml of Tri-reagent before addition of 200 µl of chloroform (Sigma-Aldrich; Steinheim, Germany). Each sample was gently mixed before incubation (for 5 minutes at 20° C.) and centrifugation (12,000 g for 15 minutes at 4° C.). The aqueous phase was transferred to a fresh tube, and 0.5 ml of isopropanol (Sigma-Aldrich) was added. Samples were allowed to stand for 5 minutes at room temperature before centrifugation at 12,000 g (for 10 minutes at 4° C.). The supernatants were removed, and the RNA pellet was washed in 75% ethanol.

Gene arrays: mRNA from T lymphocytes was analyzed by the human apoptosis expression array (R&D) as follows. To generate radiolabeled cDNA, 4 µl of human apoptosis-specific primers (R&D) were added to 4 µg of the isolated mRNA, heated in a thermal cycler at 90° C. for 2 minutes, and incubated at 42° C. for 180 minutes in the presence of reverse transcriptase buffer (50 mM Tris-HCl, 8 mM MgCl$_2$, 30 mM KCl, 1 mM DTT), 333 µM dATP, 333 µM dGTP, 333 µM dTTP, 1.67 µM dCTP, 20 U of RNasin, 20 µCi of $^{32}$P-labeled dCTP (Amersham; Freiburg, Germany), and 50 U of AMV reverse transcriptase. For hybridization, denatured salmon testis DNA (Sigma-Aldrich) was prewarmed to 65° C. in hybridization solution (0.9 M NaCl, 0.05 M sodium phosphate, 5 mM EDTA, 2% SDS, 0.1% PVP, 0.1% BSA, 0.1% Ficoll). The cDNA expression array was prehybridized in 5 ml of the prewarmed solution for 1 hour at 65° C., followed by addition of the heat-denatured labeled cDNA. After overnight hybridization at 65° C., the cDNA expression array was washed in wash solution (90 mM NaCl, 5 mM sodium phosphate, 0.5 mM EDTA, 1% SDS), air dried, and subjected to autoradiography overnight at 80° C. using Kodak BioMax MR films (Kodak; Rochester, N.Y., USA).

Preparation of cellular extracts: Cells were treated with azathioprine and 6-MP for the indicated periods of time before extraction of cellular proteins. The cells were then washed in PBS, resuspended in 1 ml of T$_{40}$E$_{10}$N$_{150}$ buffer (40 mM Tris-HCl [pH 7.9], 10 mM EDTA [pH 8.0], 150 mM NaCl), put on ice for 5 minutes, and centrifuged for 4 minutes at 4° C. at 1,000 rpm. The cell pellet was then resuspended on ice in 70 µl of buffer (10 mM HEPES [pH 8.0], 400 mM NaCl, 0.1 mM EDTA, 5% glycerol, 1 mM DTT, 1 mM PMSF) and centrifuged at 15,000 rpm for 30 minutes at 4° C. The protein concentrations in supernatants were determined with the Bio-Rad Protein Assay (Bio-Rad; Munich, Germany).

Isolation of nuclear proteins: T lymphocytes were washed twice in cold PBS and resuspended in 500 µl of buffer A (10 mM HEPES, 1.5 mM $MgCl_2$, 19 mM KCl, 0.5 mM PMSF, 1 mM DTT) followed by addition of 20 µl of Triton X-100 (Sigma-Aldrich) and incubation on ice for 5 minutes. Cells were centrifuged for 10 minutes at 4° C., followed by the resuspension of the nuclear pellet in buffer C (20 mM HEPES, 1.5 mM $MgCl_2$, 0.2 mM EDTA, 25% glycerol, 0.5 mM PMSF, 1 mM DTT). Finally, the nuclei were homogenized using mini stir bars for 1 hour at 4° C. followed by centrifugation at 15,000 rpm for 15 minutes at 4° C. The concentration of nuclear proteins in supernatants was assessed using the Bio-Rad Protein Assay.

Western blots: Equal amounts of extract (30 µg) were added to 8 µl of electrophoresis sample buffer (Firma Roth; Karlsruhe, Germany). After boiling, the extracts were loaded on 15% SDS-PAGE gels and electrophoretically separated. Proteins were transferred to nitrocellulose membranes, and detection was performed with the ECL Western blotting analysis system (Amersham). Western blots were made using the following antibodies: anti-human bcl-$x_L$ antibody (1:1000 dilution; Oncogene; Cambridge, Mass., USA), anti-human signal transducer and activator of transcription-3 (STAT-3), anti-human β-actin, anti-human ERK2 (Dianova; Hamburg, Germany), anti-human Rac1, anti-human vav, anti-human MEK, anti-human STAT3 (1:500 dilution, Santa Cruz Biotech), anti-phospho-IκB, anti-phospho-MEK (1:1000 dilution, PharMingen and R&D), and HRP-linked anti-mouse, anti-rabbit, or anti-goat Ig (1:5000 dilution; Amersham). Densitometry of Western blots was performed using the ChemiImager 5500 software (Alpha Innotech; San Leandro, Calif., USA).

Electrophoretic mobility shift assays: Electrophoretic mobility shift assays (EMSAs) were performed as described in Atreya et al., supra. Oligonucleotides for EMSA were obtained from Santa Cruz Biotech (Heidelberg, Germany). The sequences were as follows: NF-κB, 5'-AGTTGAGGG-GACTTTCCCAGGC-3' (SEQ ID NO: 1) and 3'-TCAACTC-CCCTGAAAGGGTCCG-5' (SEQ ID NO: 2); and SP-1,5'-ATTCGATCGGGGCGGGGCGAGC-3' (SEQ ID NO: 3) and 3'-TAAGCTAGCCCCGCCCCGCTCG-5' (SEQ ID NO: 4). Oligonucleotides were end labeled with [$^{32}$P]γ-ATP (>5000 Ci/mmol; Amersham; Arlington Heights, Ill., USA) using T4 polynucleotide kinase (New England Biolabs; Beverly, Mass., USA). Radiolabeled DNA (25,000 cpm) were added to the binding reaction that also contained 1 µg of synthetic DNA duplex of poly(dIdC) (Pharmacia; Piscataway, N.J., USA), 15 µg of nuclear proteins, and binding buffer (25 mM HEPES [pH 7.5], 150 mM KCl, 5 mM DTT, 10% glycerol). For supershift assays, 1 µg of antibodies specific for the p50 or p65 subunit of NF-κB (both obtained from Santa Cruz Biotech) were used. Complex formation was allowed to proceed for 30 minutes at room temperature. Finally, the complexes were separated from unbound DNA by native polyacrylamide gel electrophoresis on 5% gels. The gels were exposed to Kodak MS films on intensifying screens at –80° C.

Analysis of proteolytic activity of caspase-3, caspase-8, and caspase-9: T lymphocytes were incubated with the indicated amounts of azathioprine or 6-MP. Caspase-3 proteolytic activity was determined at day 5 by the caspase-3/CPP 32 fluorometric protease assay (Bio Source; Worcester, Mass., USA) according to the manufacturer's protocol. Caspase-8 and caspase-9 proteolytic activity were assessed in parallel by the corresponding fluorometric protease assays (Bio Source).

Measurement of the mitochondrial membrane potential: Changes in the mitochondrial membrane potential ($\Delta\Psi_m$) were estimated in primary CD4$^+$ T lymphocytes loaded with the $\Delta\Psi_m$-sensitive fluorescent dye JC-1 (Molecular Probes; Eugene, Oreg., USA). Cells were loaded with JC-1 (10 µg/ml) for 20 minutes at 37° C., rinsed with dye-free PBS, and analyzed by FACS. The fluorescence emission wavelength of JC-1 depends on the aggregation of the JC-1 molecules that in turn depend on the $\Delta\Psi_m$ (the greater the $\Delta\Psi_m$, the greater the aggregation). Changes in $\Delta\Psi_m$ were measured by monitoring JC-1 fluorescence at 590 nm. Carbonylcyanide-4-(trifluoromethoxy)-phenylhydrazone (FCCP; Biomol; Plymouth Meeting, Pa., USA), a substance that induces depolarization of the mitochondrial membrane potential, was used as a positive control. Cells were treated with FCCP (50 µM) for 18 hours.

Blocking of caspase-8 and caspase-9 activity: Primary CD4$^+$ T lymphocytes from peripheral blood were isolated as described above and stimulated with antibodies to CD3 and CD28 in the presence or absence of indicated amounts of N-acetyl-Leu-Glu-His-Asp-aldehyde (Biomol), a reversible inhibitor of caspase-9, or Ac-Ile-Glu-Thr-Asp-aldehyde (Bachem; Heidelberg, Germany), an inhibitor of caspase-8. Apoptosis was determined by FACS analysis after 5 days of cell culture.

Rac and Ras activation assays: The levels of Rac1- and Ras-bound GTP were determined by immunoblot techniques (Upstate Biotech; London, United Kindom). In brief, T cells were stimulated for indicated periods of time in the presence or absence of azathioprine, 6-MP, or 6-TG. Cell lysates were incubated with 10 µg/ml PAK-1 agarose (Rac assays) or 10 µg/mg Raf RBD agarose (Ras assay) for 60 minutes (Rac assays) or 30 minutes (Ras assays) at 4° C. Agarose beads were collected by centrifugation followed by denaturation, boiling of the samples, and SDS-PAGE analysis. Proteins were transferred to nitrocellulose membranes and incubated with 1 µg/ml murine anti-human Rac1 or anti-human Ras (clone Ras10) antibodies overnight at 4° C., followed by detection with goat anti-mouse HRP-conjugated IgG (1:1000 dilution) and the ECL detection system. To analyze the capacity of TGTP to bind to Rac1 or Ras, chemically synthesized TGTP (obtained from Jena Bioscience, Jena, Germany) was used. Recombinant Rac1 or Ras was incubated with radiolabeled GTP ([$^3$H]GTP, Amersham) and increasing amounts of TGTP (0-500 µM) followed by Rac1 and Ras pull-down through PAK and Raf RGD and analysis of [$^3$H]GTP-bound Rac1 or Ras by scintillation counting.

Immunocytochemical analysis: Immunocytochemistry was performed as described in Atreya et al., supra and Finotto et al., J. Exp. Med. 193:1247-1260 (2001)). Briefly, T cells were stimulated as above with IL-2 and antibodies to CD3 and CD28 and cultured in Lab-Tec chambered coverglass (Nunc; Wiesbaden, Germany) for 3-5 days. The cells were then fixed in 4% paraformaldehyde/PBS for 15 minutes and washed twice in 0.01M PBS/0.1% Tween. Cells were then pretreated with 3% BSA in PBS/0.1% Tween for 30 minutes at room temperature and incubated for 1 hour at room temperature with the primary antibody (1:200 dilution of rabbit anti-human Rac1 or rabbit anti-human vav; Santa Cruz Biotech; Hercules, Calif., USA, or PharMingen) in PBS/0.1% Tween. Samples without primary antibody or isotype control antibodies served as negative control and resulted in no staining. Next, samples were rinsed in PBS and incubated with Cy3-labeled goat anti-rabbit IgG antibodies (1:200 dilution; Jackson Immuno Research; Hamburg, Germany) for 1 hour at room temperature. Cells were rinsed with PBS, and nuclei were counterstained with Hoechst33342 blue for fluorescence (Molecular Probes; Burlingame, Calif., USA). Finally, cells were washed in PBS and analyzed with an Olympus Microscope. Six to ten high-power fields were finally analyzed in all patients per condition, and selected high-power fields were further analyzed by confocal laser microscopy.

Statistical analysis: Tests for significance of differences were made by Student's t test using the program StatWorks (Macintosh; Wiesbaden, Germany).

Results:

Azathioprine and its metabolites induce apoptosis of activated and preactivated CD4+ T cells from peripheral blood. Azathioprine and its metabolite 6-MP are immunosuppressive drugs that are frequently used for treatment of autoimmune and chronic inflammatory diseases such as Crohn's disease (Present et al., *N. Engl. J. Med.* 302:981-987 (1980); Sandborn et al., *Gastroenterol.* 117:527-535 (1999)). Since the regulation of T cell apoptosis plays a major role in these diseases (Scaffidi et al., *Curr. Opin. Immunol.* 11:277-285 (1999); Neurath et al., *Trends Immunol.* 22:21-26 (2001)), one aim of the present study was to determine whether azathioprine induces apoptosis of primary naive or memory CD4+ T lymphocytes upon activation through the TCR/CD3 complex and CD28. Accordingly, peripheral blood CD45RA and CD45RO CD4+ T cell subsets from healthy volunteers were isolated and stimulated with recombinant IL-2 and anti-CD3 plus anti-CD28 antibodies in the presence or absence of azathioprine and 6-MP. As shown in FIG. 1a, both azathioprine and 6-MP caused a significant induction of annexin V-positive, propidium iodide-negative naive CD45RA T cells after 5 days, suggesting that these drugs are able to induce T cell apoptosis. Similar to CD45RA T cells, azathioprine and 6-MP induced apoptosis of CD45RO memory T cells (FIG. 1b), and this effect on average was even more pronounced than in CD45RA T cells. Azathioprine and 6-MP also induced a marked increase in the number of apoptotic CD4+ T cells, as assessed by Nicoletti staining and transmission electron microscopy (FIGS. 1c and 1d).

Figure 2:
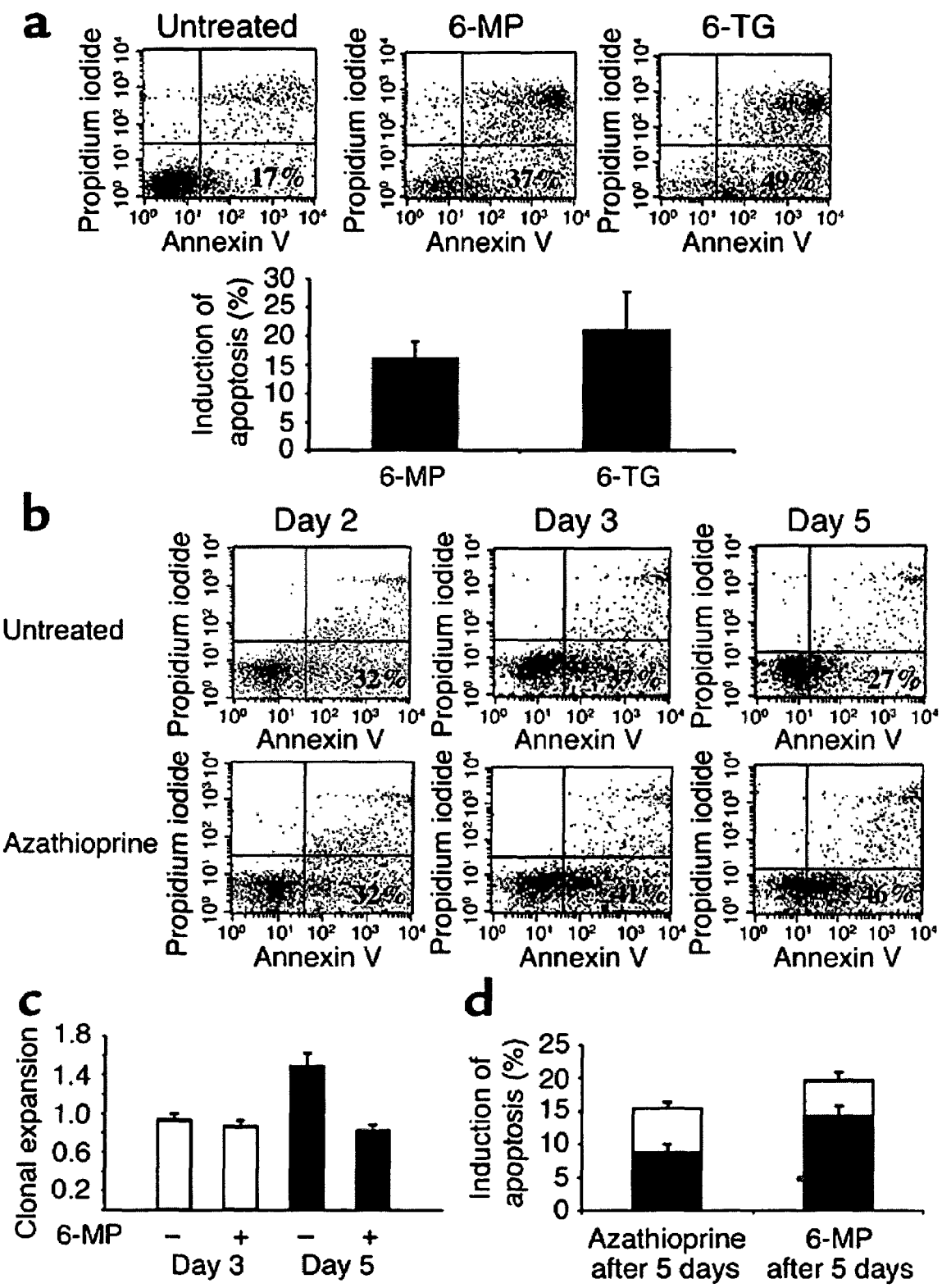
FIG. 2. (a) Peripheral blood $CD4^+$ T cells from healthy volunteers were stimulated with antibodies to CD3 and CD28 and recombinant IL-2 and cultured in the presence or absence of 6-MP and 6-TG for 4-5 days. T cell apoptosis was assessed by FACS analysis (upper panels). The average level of 6-MP- and 6-TG-specific apoptosis (induction of annexin-positive, propidium iodide-negative T cells compared with untreated cells)±SEM from four independent experiments is shown in the lower panel. (b) Kinetics of azathioprine-induced apoptosis in primary $CD4^+$ T lymphocytes. $CD4^+$ T cells were cultured in the presence or absence of azathioprine for 2-5 days as indicated. T cell apoptosis was assessed by FACS analysis at the indicated time points. (c) 6-MP suppresses clonal expansion of activated primary $CD4^+$ T lymphocytes in cell culture. $CD4^+$ T cells were cultured in the presence (+) or absence (−) of 6-MP for 3-5 days. The clonal expansion of T cells during cell culture was calculated as specified in Example 3 below. (d) $CD4^+$ T cells were cultured in the absence of azathioprine or 6-MP for 5 days, followed by addition of azathioprine or 6-MP to the cell culture for an additional 5 days. The percentage of annexin-positive, propidium iodide-negative cells was then determined at day 10 by FACS analysis. The average percentage of azathioprine- and 6-MP-specific apoptosis (induction of annexin-positive, propidium iodide-negative cells compared with untreated cells indicated by black sections of bars, induction of annexin-positive, propidium iodide-positive cells compared with untreated cells indicated by white sections)±SEM is shown in the lower panel.
Figure 6:
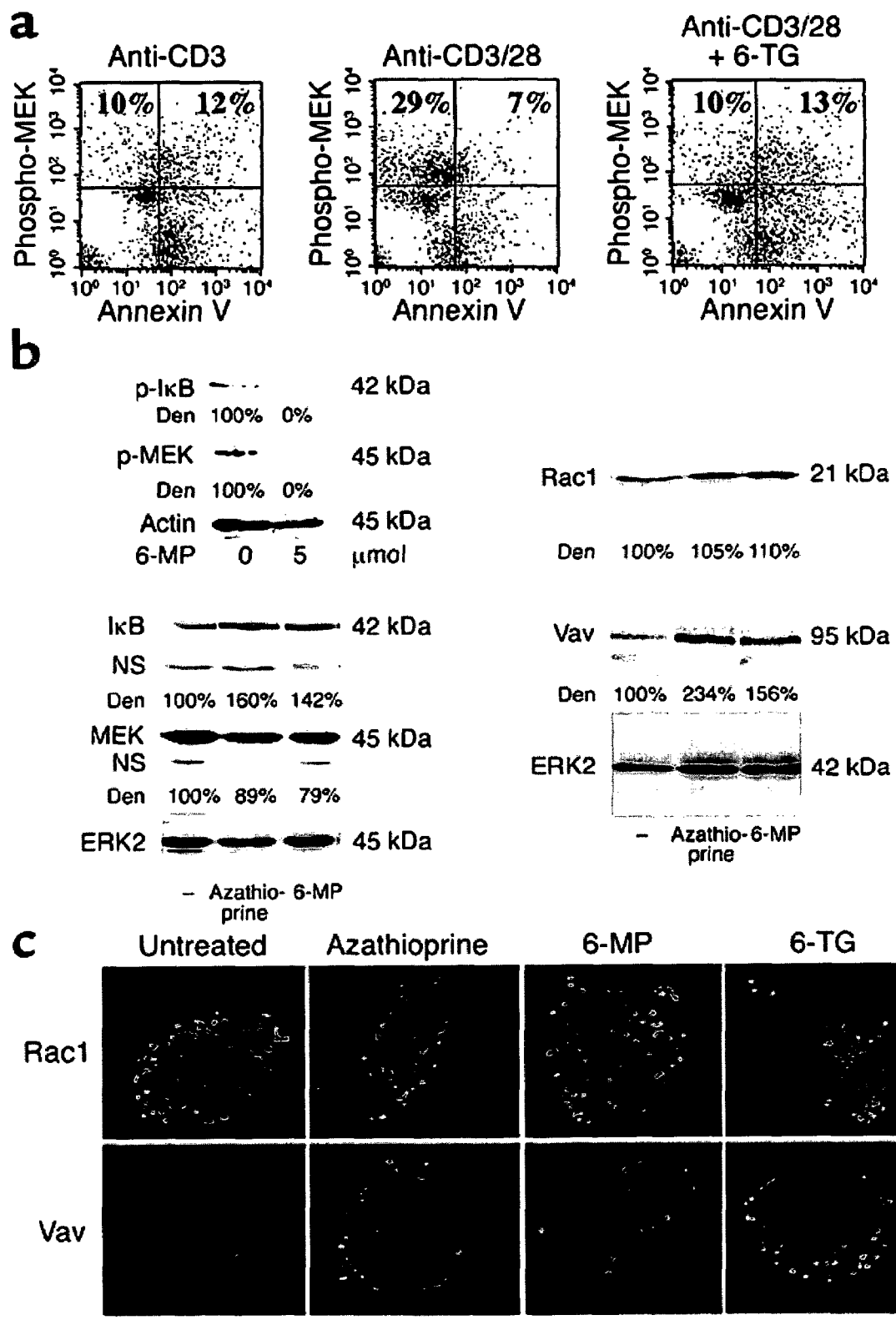
FIG. 6. Azathioprine blocks the Rac1/MEK kinase pathway. (a) Analysis of phosphorylation of MEK, a MAP kinase kinase that can be activated by MEKK (FIG. 8). Purified $CD4^+$ T lymphocytes were stimulated in the presence or absence of 6-TG. Intracellular staining for phospho-MEK by FACS analysis was made after 3 days. (b) 6-MP suppresses CD28-induced MEK and IκB phosphorylation. Purified $CD4^+$ T lymphocytes were stimulated in the presence or absence of 6-MP. Cellular proteins were isolated after 3 days and analyzed by Western blotting. The upper left panels show phospho-IκB (p-IκB) or phospho-MEK (p-MEK) activity upon 6-MP treatment. Band intensity was quantified by densitometry and normalized to actin levels. The lower left panels show IκB or MEK protein expression upon azathioprine and 6-MP treatment. Band intensity was normalized to ERK2 levels. The right panels show Rac1 and vav protein expression upon azathioprine and 6-MP treatment. Azathioprine and 6-MP treatment had little effect on Rac1 protein levels, whereas vav levels were increased in cellular extracts. Band intensity was quantified by densitometry and normalized to ERK2 levels. Den, densitometry. (c) 6-MP induces vav accumulation. $CD4^+$ T lymphocytes were stimulated in the presence or absence of azathioprine, 6-MP, or 6-TG for 5 days. Cells were immunostained with Rac1-specific antibodies and vav-specific antibodies and Cy3-labeled secondary antibodies. Nuclei were counterstained with Hoechst blue. Confocal microscopy showed that the expression of the Rac1-associated guanosine exchange factor vav was increased upon treatment with azathioprine and its metabolites, whereas Rac1 levels were nearly unchanged.

T cell apoptosis occurred at low concentrations (5 μM) of azathioprine (FIGS. 1a and 1b). This concentration of azathioprine resulted in intracellular 6-TG levels at day 5 (31.5 pmol/mg DNA at 0.5 μM azathioprine and 168 pmol/mg DNA at 5 μM azathioprine versus 0 pmol/mg DNA at 0 μM azathioprine) that were comparable to those reported in leukocytes of patients with Crohn's disease receiving long-term azathioprine or 6-MP treatment (100-2,305 pmol/mg DNA) (Cuffari et al., *Can. J. Physiol. Pharmacol.* 74:580-585 (1996)), suggesting that this concentration is relevant for therapy with azathioprine in vivo. Since 6-TG is a key metabolite with immune modifier activity of both azathioprine and 6-MP (Lennard, *Eur. J. Clin. Pharmacol.* 43:329-335 (1992)), these data were also consistent with the hypothesis that therapeutically relevant 6-TG concentrations directly induced apoptosis in azathioprine-treated primary T cells. In subsequent studies, whether 6-TG was able to induce apoptosis was tested. As shown in FIG. 2a, 6-TG induced a marked apoptosis of primary blood CD4+ T lymphocytes that was at least comparable to the effects of 6-MP, consistent with the idea that 6-TG mediates the immunosuppressive properties of azathioprine and 6-MP.

Kinetic studies showed that azathioprine and 6-MP induced T cell apoptosis after 4-5 days of cell culture only (FIG. 2b), whereas no apoptosis induction was noted during the first 2 days after administration. This data is consistent with the well-known delayed onset of clinical activity of this drug (Lennard, supra). Azathioprine-induced induction of apoptosis was accompanied by a reduction in the clonal expansion of T cells at day 5, whereas no significant changes were seen at earlier time points (FIG. 2c).

The above data suggested that azathioprine and its metabolites induce apoptosis of T lymphocytes upon stimulation with recombinant IL-2 (rIL-2) and antibodies to CD3 plus CD28. To clarify whether azathioprine can also induce apoptosis of already preactivated T lymphocytes, experiments were performed in which azathioprine or 6-MP was added after 5 days to the T cell culture. Accordingly, azathioprine or 6-MP was added at day 5 to the T cell cultures, and apoptosis was determined by annexin V/propidium iodide staining at day 10. Interestingly, azathioprine also induced apoptosis when added at this time point, suggesting that this drug is capable of inducing apoptosis in already preactivated T lymphocytes (FIG. 2d).

Figure 3:
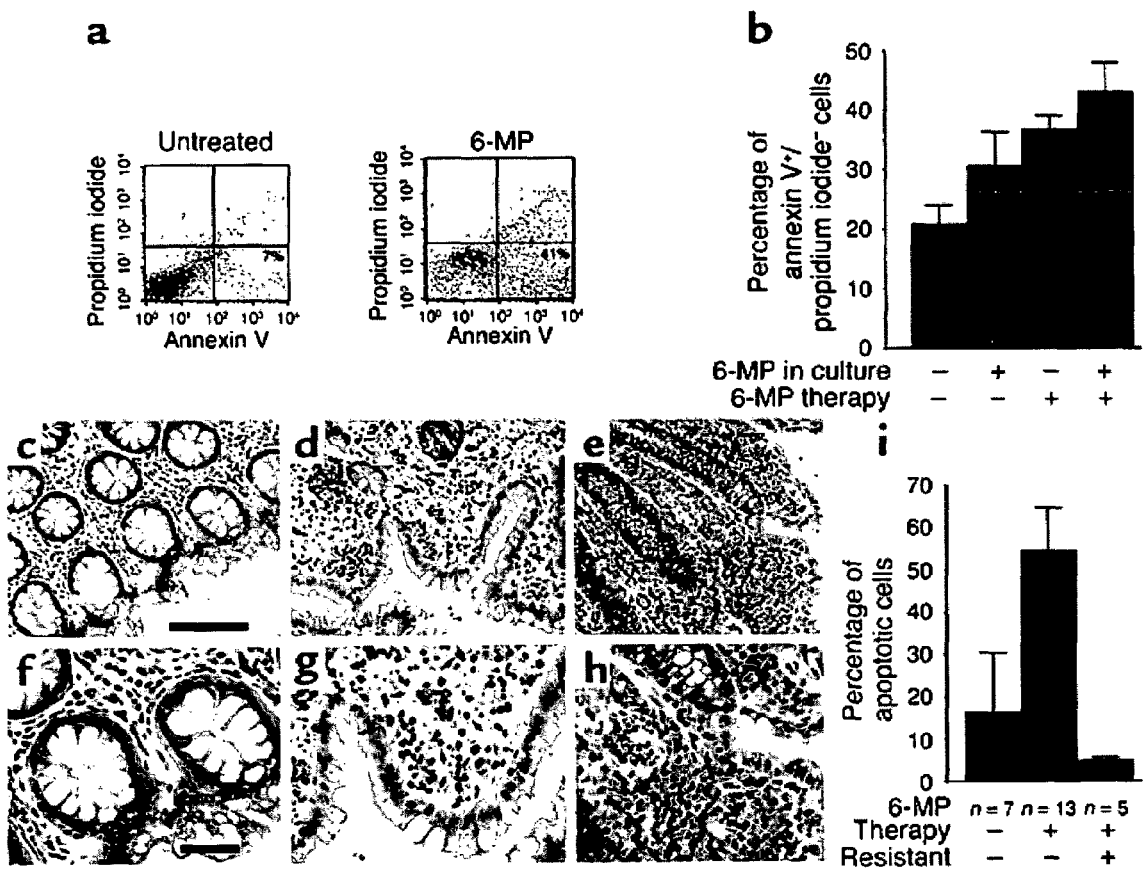
FIG. 3. Azathioprine treatment induces T cell apoptosis in IBD. (a) LPMCs were isolated and stimulated with anti-CD2/CD28 plus IL-2 in the presence or absence of 6-MP for 5 days followed by FACS analysis. (b) Peripheral blood $CD4^+$ T cells were isolated from patients with IBD receiving azathioprine/6-MP and patients with IBD before therapy and stimulated with anti-CD3/CD28 plus IL-2 in the presence or absence of 6-MP for 5 days. The number of apoptotic cells (annexin-positive, propidium iodide-negative cells) was determined by FACS analysis after 5 days and stratified according to clinical data on azathioprine therapy. Data represent mean values±SEM from eight patients with IBD per group. (c-h) TUNEL assays for the detection of apoptotic lamina propria cells in patients with IBD under azathioprine therapy. Successful azathioprine treatment associated with low-level gut inflammation was characterized by a high number of apoptotic cells (shown at low [d] and high [g] magnification) as compared with control patients with low-level gut inflammation not receiving azathioprine (c and f). In contrast, unsuccessful azathioprine treatment associated with high-level gut inflammation was characterized by a very low percentage of apoptotic cells (e and h). Data are representative of 5-13 patients per group. Magnification, ×20 (bar=100 μm) (ce) and ×40 (bar=50 μm) (f-h). (i) Quantification of the percentage of apoptotic, TUNEL-positive LPMCs in patients with IBD receiving 6-MP as compared with untreated control patients. Clinical 6-MP responsiveness was associated with a marked, significant ($P<0.01$) increase in the percentage of apoptotic LPMCs as compared with control patients with IBD not receiving 6-MP. Data are mean values±SEM of 5-13 patients per group.

Azathioprine treatment induces apoptosis of blood and lamina propria T cells in patients with inflammatory bowel diseases (IBDs): Next, we wanted to determine whether azathioprine is capable of inducing T cell apoptosis in autoimmune or chronic inflammatory diseases in vivo. In these studies, we focused on patients with IBDs such as ulcerative colitis and Crohn's disease, for whom azathioprine is considered the gold standard of immunosuppressive therapy (Present et al., supra; Podolsky, *N. Engl. J. Med.* 325:928-937 (1991)). It was found that patients treated with azathioprine or 6-MP showed a significant increase ($P<0.05$) in the number of apoptotic blood T cells when the cells were stimulated with CD28 in cell culture as compared with untreated patients before therapy (FIG. 3b). An additional treatment of T cells from 6-MP-treated patients with 6-MP in vitro did not cause a further significant increase in the percentage of apoptotic cells, suggesting that the patients were treated with sufficient dosages of 6-MP in vivo. Furthermore, we observed that 6-MP is capable of inducing apoptosis in anti-CD2 plus anti-CD28 activated lamina propria lymphocytes in ulcerative colitis (FIG. 3a), suggesting that the beneficial effect of this drug in IBD could be due to the induction of local T cell apoptosis in areas of intestinal inflammation. Consistent with this hypothesis, successful 6-MP treatment was observed in patients with IBD that led to a significant increase ($P<0.01$) in the number of apoptotic lamina propria mononuclear cells as compared with untreated patients with IBD (FIGS. 3c-3i). In contrast, 6-MP-resistant patients with IBD showed no increase in the number of apoptotic cells, suggesting that 6-MP responsiveness in patients with IBD correlates with the presence of apoptotic lamina propria cells.

Figure 4:
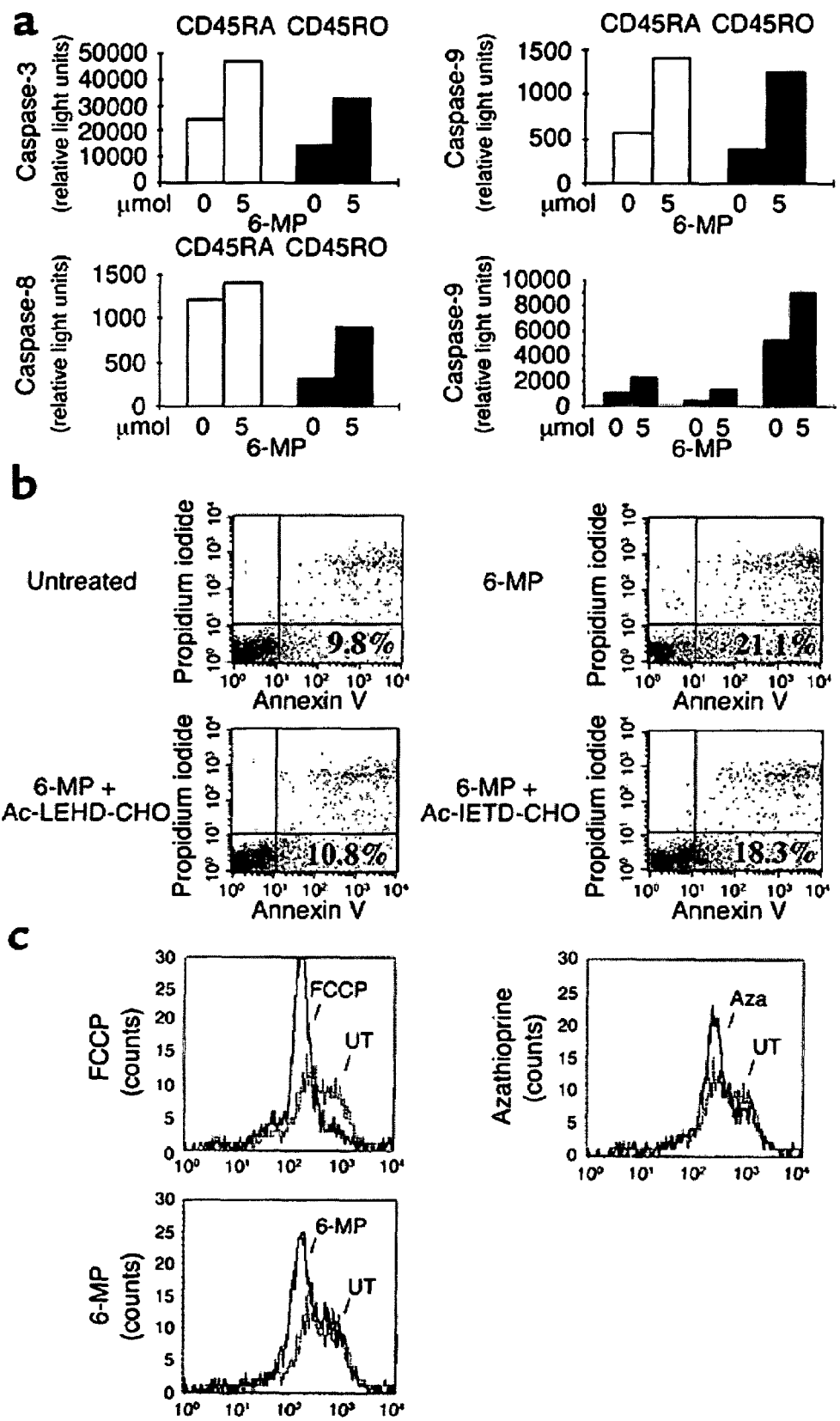
FIG. 4. Azathioprine induces a mitochondrial pathway of apoptosis. (a) Activity of caspase-3, -8, and -9 upon treatment of T cells with 6-MP. CD45RA and CD45RO T cell subsets were stimulated with antibodies to CD3 and CD28 and recombinant IL-2 for 5 days in the presence or absence of 6-MP, as indicated. There was a marked induction of caspase-9 activity upon azathioprine treatment. A second independent experiment showed similar results. Data on caspase-9 activity from three independent healthy blood donors are shown in the right lower panel. (b) Specific blockade of caspase-9 by acetyl-LEHD-CHO (Ac-LEHD-CHO) suppresses 6-MP-induced apoptosis. $CD4^+$ T lymphocytes from the peripheral blood of healthy volunteers were stimulated with antibodies to CD3 and CD28 in the presence or absence of 6-MP, 10 μM acetyl-LEHD-CHO, and 10 μm acetyl-IETD-CHO. Although acetyl-IETD-CHO had little effect, 6-MP-induced T cell apoptosis could be suppressed by acetyl-LEHD-CHO. (c) Measurement of $\Delta\Psi_m$ in primary $CD4^+$ T lymphocytes upon treatment with azathioprine, 6-MP, and FCCP (positive control). Peripheral blood $CD4^+$ T cells from healthy volunteers were stimulated with antibodies to CD3 and CD28 and recombinant IL-2 and cultured in the presence or absence of azathioprine or 6-MP for 5 days as indicated. Cells were then loaded with JC-1 for 20 minutes followed by FACS analysis to determine $\Delta\Psi_m$. Both azathioprine and 6-MP as well as FCCP led to a marked reduction of $\Delta\Psi_m$ as compared with untreated primary $CD4^+$ T cells. One representative experiment of two is shown. Aza, azathioprine; UT, untreated.

Azathioprine and its metabolites induce a mitochondrial pathway of apoptosis that is related to CD28 signaling: In initial functional studies focusing on the mechanism of azathioprine-induced apoptosis, activation of caspases in primary blood T lymphocytes by 6-MP was assessed. Accordingly, CD4+ T lymphocytes were stimulated with rIL-2 and anti-CD3 plus anti-CD28 antibodies in the presence or absence of 6-MP, and caspase activity was determined after 5 days. As shown in FIG. 4a, 6-MP led to a marked induction of both caspase-9 and caspase-3, whereas the induction of caspase-8, on average, was less pronounced. Since these data suggested that 6-MP-induced apoptosis might involve activation of a mitochondrial pathway of apoptosis involving caspase-9, consecutive studies on the role of caspase-9 in 6-MP-induced apoptosis were performed. It was found that acetyl-LEHD-CHO, a substance that, at the concentrations used, specifically blocks caspase-9 activation (FIG. 4b), suppressed 6-MP-induced apoptosis of primary T lymphocytes, whereas acetyl-IETD-CHO, a specific inhibitor of caspase-8, had lesser effects. These results indicate that 6-MP utilizes a caspase-9-sensitive mitochondrial pathway to induce T cell apoptosis upon CD28 costimulation. Consistent with this hypothesis, both azathioprine and 6-MP led to a loss of $\Delta\Psi_m$ in primary T cells (FIG. 4c) that is known to occur during mitochondrial pathways of apoptosis (Zamzami et al., *J. Exp. Med.* 181:1661-1672 (1995)).

Figure 5:
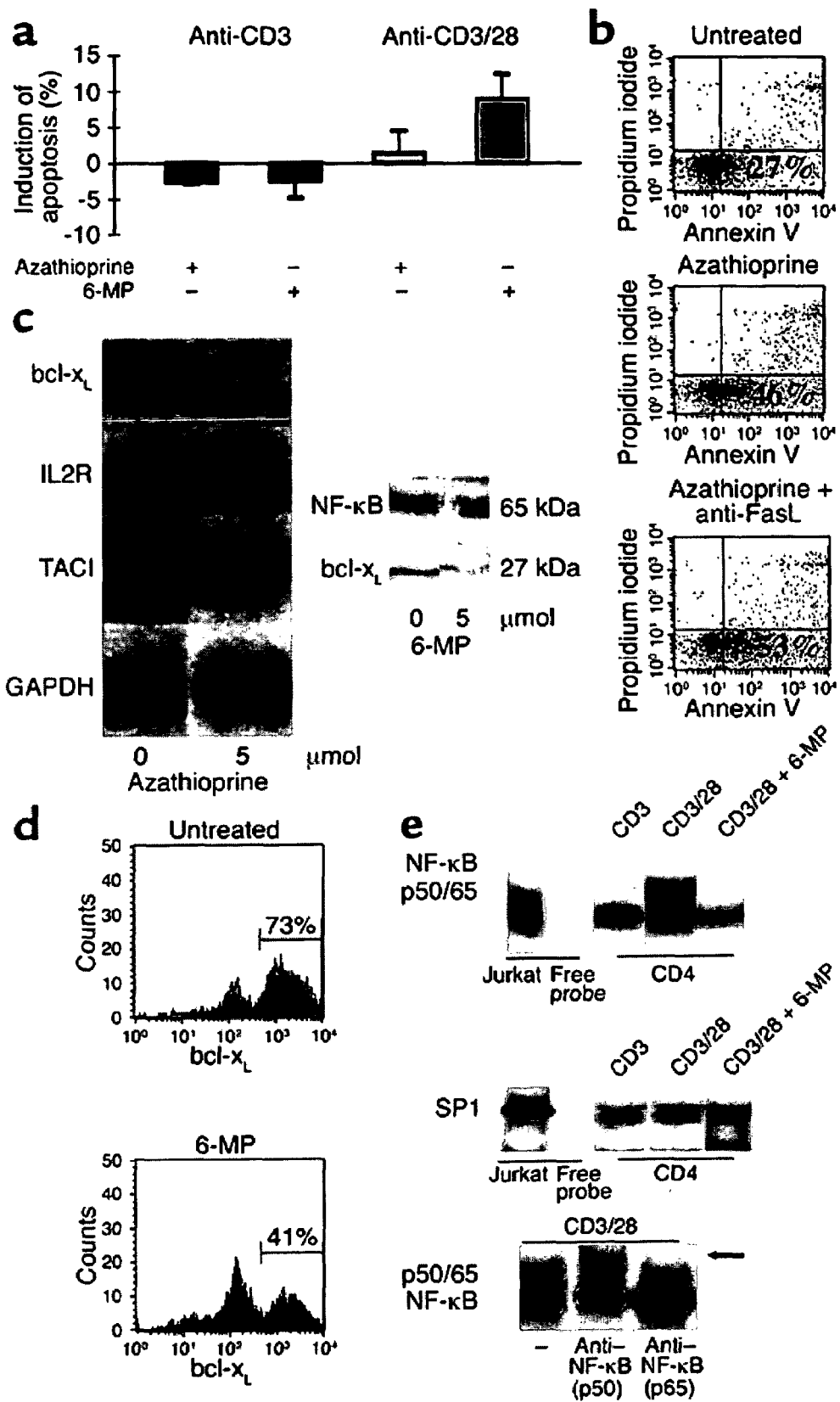
FIG. 5. (a) Azathioprine-induced apoptosis is critically dependent on costimulation with CD28. $CD4^+$ T lymphocytes were stimulated in the presence or absence of azathioprine and 6-MP, as indicated. T cell apoptosis was assessed by FACS analysis using annexin V/propidium iodide staining at day 5 of cell culture. (b) Azathioprine-induced apoptosis is independent of the CD95/CD95L system. Primary $CD4^+$ T lymphocytes were stimulated as above in the presence or absence of azathioprine and a neutralizing CD95L antibody. T cell apoptosis was assessed by FACS analysis at day 5 of cell culture. (c) The left panel shows a gene array for apoptosis-related genes in T lymphocytes. $CD4^+$ T lymphocytes were stimulated as above in the presence or absence of azathioprine. The right panel shows that 6-MP suppresses bcl-$x_L$ protein expression. Cellular proteins were isolated after 3 days of cell culture and assessed for bcl-x, or cellular NF-κB expression by Western blot analysis. (d) FACS analysis for intracellular bcl-$x_L$ expression in permeabilized lymphocytes upon 6-MP treatment. Purified $CD4^+$ T lymphocytes were stimulated in the presence or absence of 6-MP. FACS analysis for bcl-$x_L$ in permeabilized cells was performed after 5 days of cell culture. (e) 6-MP suppresses nuclear NF-κB activation. $CD4^+$ T lymphocytes were stimulated in the presence or absence of 6-MP, as indicated. Nuclear proteins were isolated after 3 days and analyzed for NF-κB (upper panel) or SP-1 (middle panel) activity by gel retardation assays (EMSAs). Nuclear extracts from PMA-stimulated Jurkat T cells served as positive controls. The lower panel represents a supershift analysis of the upper complex using extracts from anti-CD3-plus anti-CD28-stimulated primary T cells. The addition of antibodies to p50 or p65 to the EMSA reaction is indicated. 6-MP treatment led to downregulation of the NF-κB p50/p65 complex.

In subsequent studies on the mechanism of azathioprine-induced apoptosis, the requirement of T cell costimulation with CD28 for azathioprine- and 6-MP-induced apoptosis was determined (FIG. 5a). It was found that azathioprine and 6-MP induced apoptosis when primary blood $CD4^+$ T lymphocytes were stimulated through the TCR/CD3 complex plus CD28, whereas no apoptosis was seen when cells were stimulated with anti-CD3 antibodies alone (FIG. 5a), demonstrating a selectivity of this drug for costimulated T lymphocytes. Based upon this requirement for CD28 costimulation, the CD28-related signaling events involved in azathioprine- and 6-MP-induced apoptosis were further investigated.

CD28 costimulation has been shown to affect both the death receptor and the mitochondrial pathways of apoptosis induction (Kirchhoff et al., *Eur. J. Immunol.* 30:2765-2774 (2000)). Given its implication in activation-induced cell death of T cells, the possible contribution of the CD95L/CD95 interaction to the apoptotic effect of azathioprine was first studied. Interestingly, specific blockade of the CD95L/CD95 system by CD95L-neutralizing antibodies did not affect azathioprine-induced apoptosis of anti-CD3- plus anti-CD28-stimulated primary blood $CD4^+$ T lymphocytes (FIG. 5b), indicating that azathioprine induces T cell apoptosis through a CD95-independent pathway.

To identify candidate genes that may be responsible for azathioprine-induced apoptosis, the gene products that are induced or suppressed by azathioprine during T cell apoptosis were characterized. In these studies, gene arrays that included various genes involved in apoptosis were used (FIG. 5c). It was found that azathioprine strongly suppressed $bcl-x_L$ mRNA expression in anti-CD3- plus anti-CD28-activated T lymphocytes, whereas mRNA expression of various other genes such as IL-2R, TACI, and GAPDH was not affected. Furthermore, $bcl-x_L$ protein expression in activated T cells was strongly suppressed by azathioprine and 6-MP (FIGS. 5c and 5d), indicating that azathioprine induces suppression of $bcl-x_L$ mRNA and protein levels in activated primary $CD4^+$ T lymphocytes. Since $bcl-x_L$ expression in T lymphocytes is known to be controlled by the transcription factor NF-κB (Noel et al., supra; Khoshnan et al., *J. Immunol.* 165:1743-1754 (2000); Tuosto et al., *Eur. J. Immunol.* 30:2445-2454 (2000)), whether CD28-induced activation of NF-κB was altered in primary T lymphocytes upon 6-MP treatment was determined. As shown in FIG. 5e, 6-MP suppressed CD28-induced activation of NF-κB p50/p65. In particular, 6-MP downregulated the nuclear expression of the p65 subunit of NF-κB that has been implicated in antagonizing T cell apoptosis.

Azathioprine causes a specific blockade of the Rac1 activation pathway in primary T lymphocytes: Since activation of NF-κB upon CD28 costimulation is mediated by phosphorylation and degradation of IκB (Tuosto et al., supra), IκB phosphorylation in 6-MP-treated cells was determined. It was found that IκB phosphorylation was suppressed by 6-MP treatment of T cells, whereas IκB protein expression levels remained unchanged (FIG. 6b), indicating that CD28-mediated NF-κB activation through phosphorylation and degradation of IκB is a target of this drug. Since IκB phosphorylation in CD28-stimulated primary T cells is mediated by the vav/Rac1/MEK kinase (MEKK) activation pathway (Tuosto et al., supra), the potential modulation of this pathway by azathioprine and 6-MP was assessed. Interestingly, azathioprine and its metabolites suppressed MEK phosphorylation, but the expression levels of MEK were nearly unchanged (FIGS. 6a and 6b). Furthermore, the expression of Rac1 was not significantly suppressed by azathioprine and 6-MP, whereas both drugs induced the expression of the Rac1-activating guanosine exchange factor vav (FIGS. 6b and 6c), a regulatory protein previously shown to be a key target for CD28 signaling (Chiang et al., *Nature* 403:216-220 (2000); Krawczyk et al., *Immunity* 13:463-473 (2000); Raab et al., *Immunity* 15:921-933 (2001)).

Figure 7:
FIG. 7. (a) Rac1 activation assay in activated primary T cells. Purified $CD4^+$ T lymphocytes were stimulated with IL-2 and antibodies to CD3 or IL-2 plus antibodies to CD3 and CD28 for 3 days. GTP-bound Rac1 (Rac1-GTP) was analyzed using PAK to determine Rac1 activation. CD28 costimulation led to induction of Rac1 activation in primary T cells. (b) Azathioprine and 6-MP suppress Rac1 activation. Purified $CD4^+$ T lymphocytes were stimulated in the presence or absence of azathioprine or 6-MP for 3 days, as indicated. GTP-bound Rac1 was analyzed using PAK to determine Rac1 activation. Azathioprine treatment led to a reduction of CD28-dependent Rac1 activation. One representative experiment out of five is shown. (c) 6-MP and 6-TG fail to modulate Ras activation. GTP-bound Ras (Ras-GTP) was analyzed using Raf RGD to determine Ras activation. Azathioprine and its metabolites did not affect Ras activation. One representative experiment of three is shown. (d) Downregulation of STAT-3 in primary T cells upon treatment with azathioprine or 6-MP. Purified $CD4^+$ T lymphocytes were stimulated in the presence or absence of azathioprine and 6-MP for 3 days, as indicated. Since Rac1 binds and activates STAT-3, GTP-bound Rac1 was obtained using PAK, and STAT-3 levels were determined by immunoblotting. (e) Competition of GTP binding to Rac1 or Ras by 6-Thio-GTP (TGTP). Recombinant Rac1 or Ras was incubated with radiolabeled GTP ($[^3H]$ GTP) and increasing amounts of chemically synthesized 6-Thio-GTP (0-500 μM). Next, Rac1 was obtained using PAK-1 agarose, followed by analysis of $[^3H]$GTP-bound Rac1 by scintillation counting. Similarly, Ras was obtained using Raf RGD agarose followed by analysis of [$^3$H]GTP-bound Ras by scintillation counting. 6-Thio-GTP led to a concentration-dependent suppression of [$^3$H]GTP-bound Rac1 but had little effect on [$^3$H]GTP-bound Ras.

CD28 costimulation induced Rac1 activation in primary T cells (FIG. 7a) was strongly suppressed by azathioprine, 6-MP, or 6-TG treatment, as shown by a reduction of GTP-bound Rac1 (FIG. 7b). Since Rac1 is known to bind and activate STAT-3 (Simon et al., *Science* 290:144-147 (2000)), a key factor for regulating bcl-x, expression in T cells (Atreya et al., supra), Rac1-bound STAT-3 was also assessed and was observed to be reduced in azathioprine-treated T cells (FIG. 7d). Rac1 activation upon CD28 costimulation thus appears to control both the NF-κB and STAT-3 activation pathways that are known to prevent T cell apoptosis upon CD28 costimulation, and azathioprine and its metabolites suppress this activation pathway.

To exclude a general inhibitory effect of azathioprine and its metabolites on the activation of GTPases, the activation of Ras that is known to occur upon CD3/TCR stimulation of T cells was determined. It was found that the activation of Ras was virtually unaffected (FIG. 7c), indicating a specific inhibition of Rac1 activation by azathioprine. This marked specificity pointed to the potential direct binding of an azathioprine metabolite to Rac1. Indeed, 6-TG was detected in Rac1 pull-downs from primary T cells upon azathioprine treatment (approximately 120 pg of 6-TG per microgram), indicating that azathioprine-generated TGTP can directly bind to Rac1 in vivo. Consistently, TGTP was able to bind to recombinant Rac1 under in vitro conditions (although with lower affinity than GTP) (FIG. 7e). Furthermore, TGTP did not significantly compete with GTP for recombinant Ras, indicating that TGTP may bind to selected GTPases only.

Taken together, these data show that azathioprine and its metabolites target CD28-mediated signaling in primary T cells by specifically suppressing the activation of the GTPase Rac1 through TGTP, leading to a mitochondrial pathway of apoptosis (FIG. 8).

Discussion:

In the present study, a unique and unexpected role for azathioprine and its metabolites in the control of T cell apoptosis by modulation of Rac1 activation upon CD28 costimulation was identified. Specific blockade of Rac1 activation is achieved by azathioprine-generated TGTP that binds to Rac1 instead of GTP. Consequently, the activation of Rac1 target genes such as MEK, NF-κB, and $bcl-x_L$ is suppressed by azathioprine, leading to a mitochondrial pathway of apoptosis. Azathioprine thus converts a costimulatory signal into an apoptotic signal by modulating Rac1 activity. These findings explain the beneficial immunosuppressive effects of azathioprine and have important implications for the design of novel specific therapies for organ transplantation, autoimmune diseases, and autoimmune diseases such as IBD.

Since unchecked proliferation of lymphocytes may provoke the risk of developing chronic inflammatory or autoimmune diseases, the immune system controls efficient elimination of activated lymphocytes in a process known as apoptosis. This is particularly important for the mucosal immune system, since a resistance of lamina propria cells to apoptosis may lead to chronic inflammatory responses in the gut. It is shown in the present study that azathioprine induces T cell apoptosis (e.g., CD45RO memory T cells). Since CD45RO T lymphocytes are considered to be key effector cells in IBD, the excellent therapeutic efficacy of azathioprine in these diseases could be due to the induction of local T cell apoptosis. This hypothesis is supported by the finding that successful azathioprine treatment in patients with IBD leads to an increased number of apoptotic T cells in the peripheral blood and the lamina propria. This mechanism of action based on apoptotis induction of activated T cells also explains why azathioprine is effective in both Crohn's disease and ulcerative colitis, although both diseases seem to have a different pathogenesis and are associated with a different T cell cytokine profile (Breese et al., *Immunology* 78:127-131 (1993), Plevy et al., *J. Immunol.* 159:6276-6282 (1997), Neurath et al., *Trends Immunol.* 22:21-26 (2001)).

The induction of apoptosis by azathioprine was critically dependent on T cell costimulation with CD28, which is known to inhibit TCR-induced apoptosis during a primary T cell response by activation of the antiapoptotic bcl-$x_L$ protein (Boise et al., *Curr. Opin. Immunol.* 7:620-625 (1995); Mueller et al., *J. Immunol.* 156:1764-1771 (1996)). Interestingly, azathioprine downregulates bcl-x, expression at the mRNA and protein levels, indicating that this drug blocks a key regulatory pathway in CD28 signaling. The fact that azathioprine regulates bcl-$x_L$ expression indicates that azathioprine regulates a mitochondrial pathway of apoptosis. Indeed, azathioprine-mediated apoptosis led to downregulation of the mitochondrial membrane potential and was suppressed by a specific inhibitor of caspase-9.

The MEK/NF-κB signaling pathway that is known to induce bcl-$x_L$ expression upon CD28 costimulation in primary T cells was also analyzed (Tuosto et al., supra). It was found that azathioprine and its metabolites suppressed MEK and NF-κB activation through IκB phosphorylation, although IκB and MEK protein levels were nearly unaffected. These data indicated that the suppression of the MEK/NF-κB signaling pathway by azathioprine is mediated by an unexpected specific mechanism involving an azathioprine metabolite rather than by azathioprine-induced suppression of protein production. Indeed, the azathioprine metabolite TGTP directly binds to Rac1, a Rac GTPase that is known to play a key role in CD28 signaling and MEK/NF-κB activation in T cells (Marinari et al., *Eur. J. Immunol.* 32:447-456 (2002); Gomez et al., *Nat. Immunol.* 1:348-352 (2000); Joneson et al., *Mol. Cell. Biol.* 19:5892-5901 (1999)). Furthermore, the levels of vav1, a CD28-responsive guanosine exchange factor for Rac1 whose activity is suppressed by the adapter protein Cb1-b (Chiang et al., *Nature* 403:216-220 (2000); Krawczyk et al., *Immunity* 13:463-473 (2000); Raab et al., *Immunity* 15:921-933 (2001)), were upregulated by azathioprine treatment. This finding is consistent with a compensatory upstream mechanism to achieve Rac1 activation in primary T cells upon administration of azathioprine.

Rac proteins play a major role in T cell development, differentiation, and proliferation (Gomez et al., supra; Joneson et al., supra; Li et al., *Science* 288:2219-2222 (2000)). Whereas dominant positive Rac mutations have been associated with increased cell proliferation and tumors, functionally inactive Rac mutations are associated with immunodeficiencies in humans (Williams et al., *Blood* 96:1646-1654 (2000)). Azathioprine-mediated suppression of Rac1 activation in T cells was mediated by direct binding of an azathioprine metabolite (TGTP) to Rac1 instead of GTP. Although the precise mechanism by which binding of TGTP suppresses Rac1 activation in T cells remains to be determined, the function of another GTPase (Ras) was not inhibited by azathioprine and its metabolites. As such, these findings are consistent with a model in which the specificity of the TGTP-induced blockade of Rac1 function is related to the structure of the Rac1 protein. In any case, azathioprine specifically blocked the Rac1-mediated activation of NF-κB and STAT-3 in primary T cells that mediate bcl-$x_L$ activation upon CD28 costimulation and therefore provide an important antiapoptotic signal in anti-CD28-stimulated T lymphocytes (FIG. 8). The CD28 signaling pathway, however, is not only important for the initial activation of T cells but also for maintaining their viability and responsiveness during a persistent immune response (Noel et al., supra; Mueller et al., supra). Azathioprine-induced suppression of CD28 signaling events may be particularly important for the mechanism of action of this drug, since it is frequently used in chronic inflammatory diseases in which repeated antigen-specific stimulation of effector T cells occurs and in which elimination of effector T cells is needed (Boirivant et al., *Gastroenterol.* 116:557-565 (1999), Neurath et al., supra). Consistent with this idea, azathioprine can also induce apoptosis of T lymphocytes that were preactivated with CD28.

Taken together, the present study identifies a unique and novel molecular mechanism of action of azathioprine on the basis of the suppression of Rac1 activation. Further studies showed that azathioprine-induced suppression of Rac1 activation leads to suppression of bcl-$x_L$ expression (through blockade of NF-κB and STAT-3 activation) and a mitochondrial pathway of T cell apoptosis. Thus, azathioprine-induced immunosuppression is mediated by suppression of Rac1 activation and the consecutive induction of T cell apoptosis. Azathioprine-induced apoptosis affects mainly CD45RO effector T cells upon costimulation with CD28, indicating that azathioprine may be particularly effective in eliminating pathogenic memory T cells in autoimmune and chronic inflammatory diseases. These data have important implications for the design of novel and more specific therapies for autoimmune and inflammatory diseases. In particular, TGTP derivatives with higher affinity to Rac1 may be useful to achieve more powerful immunosuppression in autoimmune diseases, inflammatory diseases, and organ transplantation.

Example 2

Highly Sensitive and Specific Determination of the Intracellular Concentrations of 6-thioguanosine Mono-, Di-, and Triphosphates in Red Blood Cells of Patients Undergoing Azathioprine Therapy This example illustrates a novel assay for comprehensively quantifying the individual thioguanosine metabolites, i.e., 6-thioguanosine mono- (TGMP), di- (TGDP), and triphosphate (TGTP), in the red blood cells (RBC) of patients undergoing azathioprine therapy.

Methods:

The thioguanosine phosphates were extracted from RBC by a simple extraction procedure and subsequently oxidized to the corresponding 6-sulfonates. Separation was achieved by isocratic reversed phase HPLC with an ion pairing reagent and detection by fluorescence. Stability of the nucleosides during sample work-up was thoroughly investigated.

Chemicals and Preparation of Calibrators:

The reference compounds TGMP, TGDP, TGTP, and TdGTP were provided by Jena Bioscience (Jena, Germany). 6-thioguanosine and 6-thioguanine (6TG) were purchased from Sigma.

Methanol, acetonitrile, and dichloromethane were provided from Roth (Germany, HPLC grade). 1,4-Dithio-D/L- threitol (DTT) was purchased from Applichem; EDTA (disodium salt, dihydrate) from Sigma; and tetrabutylammonium hydrogensulfate (TBAHS) from Fluka. All other chemicals were purchased from Merck (Darmstadt, Germany). EDTA was prepared as a 50 mM solution and adjusted to pH 10.5 with 5 N NaOH. Solutions of DTT (30 mg/ml in 50 mM EDTA pH 10.5) were prepared freshly prior to any experiment. Pure water was obtained from a Milli-Q system (Millipore).

Solutions of 6-thioguanosine and 6-thioguanine (6TG) were prepared as described in Iven, *Clin. Pharm.* 14:89-95 (1996). Stock solutions of the thioguanosine nucleotides were prepared in water at a final concentration of 10 mM and stored at −20° C. Working solutions at final concentrations of 10 μM and 1 μM were obtained by dilution with EDTA (50 mM) and kept at 4° C. Final concentrations were determined by quantification of 6TG following acid hydrolysis. Aliquots of the solutions were diluted to a volume of 150 μl with potassium phosphate buffer (20 mM, pH 7.4) and subsequently treated with 6.4 μl of 70% perchloric acid for 60 min at 95° C. 41 μl of 2.5 M potassium bicarbonate was added to the cooled samples followed by centrifugation to separate from precipitate. Oxidation and HPLC analysis was performed as described below. Quantification was achieved by external calibration using 6TG in the range of the expected concentrations. Standard curves were obtained by linear regression using peak areas versus concentrations.

Preparation of Erythrocyte Lysate

Blood samples were collected into EDTA tubes and immediately cooled on ice. To isolate packed RBC, the blood was centrifuged for 10 minutes at 3000 rpm and the plasma was discarded. The remaining RBC were washed once with the same volume of 0.9% sodium chloride and the supernatant removed. An aliquot of 100 μl was suspended in 200 μl of 0.9% sodium chloride for determination of hemoglobin and cell count. The remaining sample was immediately frozen at −80° C. until analysis.

Sample Preparation

To a mixture of 140 μl of EDTA and 10 μl of DTT, 100 μl of RBC, thawed immediately before use, were added. After thorough mixing and a short waiting period of 5 min, proteins were precipitated by the addition of 100 μl of methanol, followed by the addition of 250 μl of water and 500 μl of DCM. After vortex mixing and centrifugation for 10 min at 10,000 g, 500 μl of the upper aqueous layer was transferred into new Eppendorf tubes.

Aliquots of the extract were oxidized according to the method described in Finkel, *J. Pharm. Sci.* 64:121-122 (1975) and Rabel et al., *Anal. Biochem.* 224:315-322 (1995). Briefly, 150 μl of the aqueous supernatant was mixed with 10 μl of 1 M sodium bicarbonate buffer (pH 10.1) followed by 100 μl of 0.24% $KMnO_4$. The oxidation procedure was terminated after 5 min by addition of 10 μl of 30% $H_2O_2$. After centrifugation, an aliquot of 25 μl was diluted with water (1:1, v/v), and 20 μl of this mixture were used for HPLC analysis. Patients samples were always analyzed in duplicate.

HPLC Instrument and Chromatographic Separation

The HPLC system consisted of an automated system with a Shimadzu LC-9A pump, an autoinjector (Shimadzu SIL-9A), and a fluorescence detector (Shimadzu RF535, xenon lamp, excitation 315 nm, emission 390 nm). The samples were separated by isocratic elution on a Nucleosil 100-5-C18 column (250×4.6 mm ID, Macherey & Nagel) protected by a 5 μm precolumn (Hypersil ODS or Prontosil C18). The HPLC run was performed at 30° C. (Thermostat Jetstream 2, Bischoff). The mobile phase consisted of 84% potassium phosphate buffer (20 mM) adjusted to pH 6.8 after dissolving tetrabutylammonium hydrogensulfate (5 mM concentration referred to the aqueous phase) and of 16% acetonitrile (v/v). Typical flow rate was 0.7 to 0.9 mL/min with a run time of 45 min. HPLC chromatograms were acquired and analyzed with the Galaxie chromatography data system (Varian; Darmstadt, Germany).

Calibration

Calibration samples and controls were prepared as described in Rabel et al., supra, with minor modifications. Known amounts of 6-thioguanosine phosphates were added to a mixture of EDTA and 10 μl of DTT to give a final volume of 150 μl. Finally, 100 μl of blank RBC were added and the mixture thoroughly homogenized by vortex mixing. Sample preparation was performed as described above. Calibration curves covered the range of 10 to 50 pmol for TGMP, 10 to 100 pmol for TGDP, and 20 to 400 pmol for TGTP per sample referred to 100 μl of packed blank RBC. Standard curves were obtained by linear regression using peak areas versus concentrations. Because of the partial conversion of TGDP to TGTP and vice versa, both peak areas were summed up. In addition, combinations of 5 to 20 percent of TGDP per sum of TGDP and TGTP were prepared.

Method Validation

Assay accuracy and precision was determined by analyzing blank RBC spiked separately with three different concentrations of each of the thioguanosine phosphates. For intraday analysis, 5 replicates at each concentration were used; for interday analysis, five replicates on 3 different days were used. Assay accuracy was determined as the measured concentration relative to the added concentration in percent. Imprecision was calculated by the CV.

Extraction efficiencies were determined separately for each of the three compounds by comparing the peak areas from spiked RBC samples to those from samples prepared with 0.9% saline.

The percentage of conversion of TGDP to TGTP and of TGTP to TGDP was assessed using three sets of TGDP and TGTP calibrators prepared with different RBC.

Stability of Thioguanosine Phosphates

Stability of the thioguanosine phosphates in blood samples was examined by storing blood samples from patients for up to 5 days at ambient temperature. RBC were isolated after the specified storage time and frozen at −80° C. until analysis.

Stability during storage of RBC at −80° C. was investigated in samples from 18 patients. RBC which were analyzed within one week after isolation were compared with RBC stored for up to 14 weeks.

Stability of thioguanosine phosphates in extracted samples was investigated by storage of extracted samples from 12 patients before oxidation and after oxidation for 14 days and comparing the results with the same samples analyzed immediately after oxidation.

Results:

HPLC Method

Figure 9:
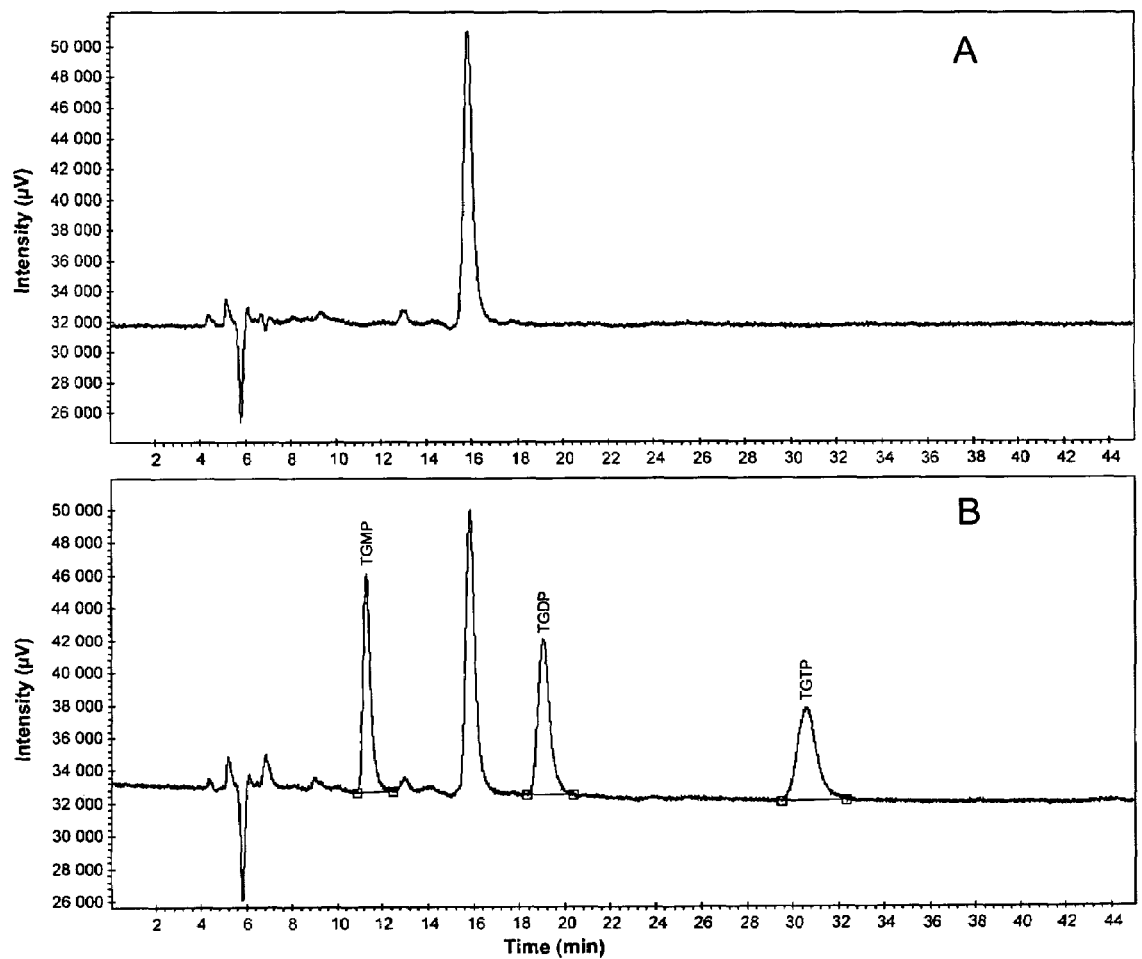
FIG. 9 shows representative chromatograms of (A) blank RBC and (B) blank RBC spiked with 100 pmol each of TGMP, TGDP and TGTP.

Separation of the oxidized thioguanosine phosphates was achieved by reversed phase ion pairing HPLC on a C18 column under isocratic conditions. A critical point was interference of an intense matrix peak with TGMP and TGDP, which was dependent on the C18 material used. Typical chromatograms of blank RBC and RBC spiked with the thioguanosine phosphates are shown in FIG. 9 and demonstrate the separation of the analytes from the large matrix peak.

With the HPLC method used, 9-O-ribosyl-analogues will co-elute with the corresponding 2'-deoxy ribosyl analogues as has been experienced with TdGTP as reference compound which eluted with identical retention time compared to TGTP when measured as 6-sulfonate.

Assay Validation

The method was linear over the whole concentration range from 10 to 50 pmol for TGMP, 10 to 100 pmol for TGDP, and 20 to 400 pmol for TGTP per sample referred to 100 µl of packed blank RBC.

The limit of detection was 5 pmol/100 µl of RBC when defined as 3 times the signal-to-noise ratio and injection of a 10 µl aliquot diluted with an equal volume of water. Mean extraction efficiencies were 95.0, 98.0, and 87.8% for TGMP, TGDP, and TGTP, respectively, in the concentration ranges selected.

Data on intraday and interday precision and accuracy are summarized in Table 1. The three thioguanosine phosphates, TGMP, TGDP, and TGTP, were assayed separately. In samples containing TGDP or TGTP, peak areas of these two nucleotides were summed up as partial interconversion occurred. For all concentrations including the limit of quantification (10 pmol), the accuracy, expressed as concentration found/concentration added×100% was between 90.5% and 106.5%. The CVs were below 10% at all concentrations. In samples spiked with mixtures of the phosphates, precision also was good, with CVs below 10% and the accuracy referring to the sum of the phosphates was between 90.1% and 103.6%. Repeatability of different patient samples was also very consistent with CVs below 8% for all nucleotides and below 2.5% for the percentage of TGTP (Table 2).

was observed. In more than 10 different blank RBC used, conversion of TGDP to TGTP accounted for about 6-15%, and conversion of TGTP to TGDP varied from 6-20%. As an example, conversion rates of spiked samples from three healthy volunteer are shown in Table 3. Conversion of TGDP to TGTP is nearly identical for all three subjects with 7-8%. For TGTP, subjects 1 and 2 show only small conversion rates of 9.7% or 6.1%, while in a third sample the conversion accounted for nearly 18%. In 0.9% NaCl as a comparison, TGDP did not show any conversion. In saline samples spiked with TGTP, about 5% TGDP was found after sample work-up, which is nearly identical to the original TGDP content in the TGTP standard, determined to be 3.8%.

TABLE 3

Interconversion of TGDP and TGTP.

| Calibrator added | | RBC 1 | RBC 2 | RBC 3 | 0.9% NaCl |
|---|---|---|---|---|---|
| TGDP | Area % TGDP, mean (n = 6) | 91.6 | 92.6 | 92.8 | 100.0 |
| TGTP | Area % TGTP, mean (n = 6) | 90.3 | 93.9 | 82.2 | 95.6 |

Area percent TGTP or TGDP refers to the sum of areas of TGTP and TGDP and is calculated as area calibrator × 100/(area TGTP + area TGDP).

Stability of 6-Thioguanine Nucleotides in Patient Samples

Stability of the nucleotides was investigated in blood samples obtained from patients under azathioprine therapy. Storage of blood samples on ice before isolation of RBC showed no change for the first 6 hours but after one day of

TABLE 1

Precision and accuracy for the determination of 6-thioguanosine 5'-phosphates in RBC.

| Calibrator | Concentration added (pmol/100 µl RBC) | Intraday (n = 5) Concentration found (pmol/100 µl RBC) | CV (%) | Accuracy (%) | Interday (n = 15) Concentration found (pmol/100 µl RBC) | CV (%) | Accuracy (%) |
|---|---|---|---|---|---|---|---|
| TGMP | 20 | 18.1 | 7.0 | 90.5 | 19.5 | 7.3 | 97.6 |
|  | 40 | 40.1 | 3.3 | 100.3 | 40.8 | 3.0 | 102.1 |
|  | 60 | 61.0 | 2.1 | 101.7 | 60.8 | 2.1 | 101.4 |
| TGDP | 15 | 16.04 | 5.7 | 106.9 | 14.9 | 6.9 | 99.3 |
|  | 30 | 30.4 | 3.4 | 101.3 | 30.3 | 2.5 | 101.0 |
|  | 50 | 50.9 | 2.0 | 101.8 | 50.2 | 2.2 | 100.4 |
| TGTP | 50 | 51.7 | 1.7 | 103.4 | 49.7 | 4.1 | 99.4 |
|  | 150 | 151.3 | 0.6 | 100.9 | 149.0 | 3.7 | 99.3 |
|  | 300 | 300.1 | 2.0 | 100.4 | 300.4 | 1.5 | 100.2 |

The interday values were determined with 3 different blank RBC in three consecutive series separately for each of the individual thioguanosine metabolites.

TABLE 2

Repeatability for the determination of thioguanosine phosphates in RBC of patients.

| Patient | TGMP mean (pmol/ml) | CV, (%) | TGDP mean (pmol/ml) | CV, (%) | TGTP mean (pmol/ml) | CV, (%) | TGDP + TGTP mean (pmol/ml) | CV, (%) | Percentage TGTP mean | |
|---|---|---|---|---|---|---|---|---|---|---|
| A | — |  | 47.5 | 7.9 | 329 | 6.6 | 376 | 5.6 | 87.4 | 2.4 |
| B | 286 | 5.5 | 269 | 4.9 | 2190 | 5.0 | 2460 | 5.0 | 88.4 | 1.7 |
| C | — |  | 87 | 6.0 | 1190 | 5.6 | 1280 | 5.6 | 93.2 | 0.3 |

Conversion of TGDP into TGTP and Vice Versa

Figure 10:
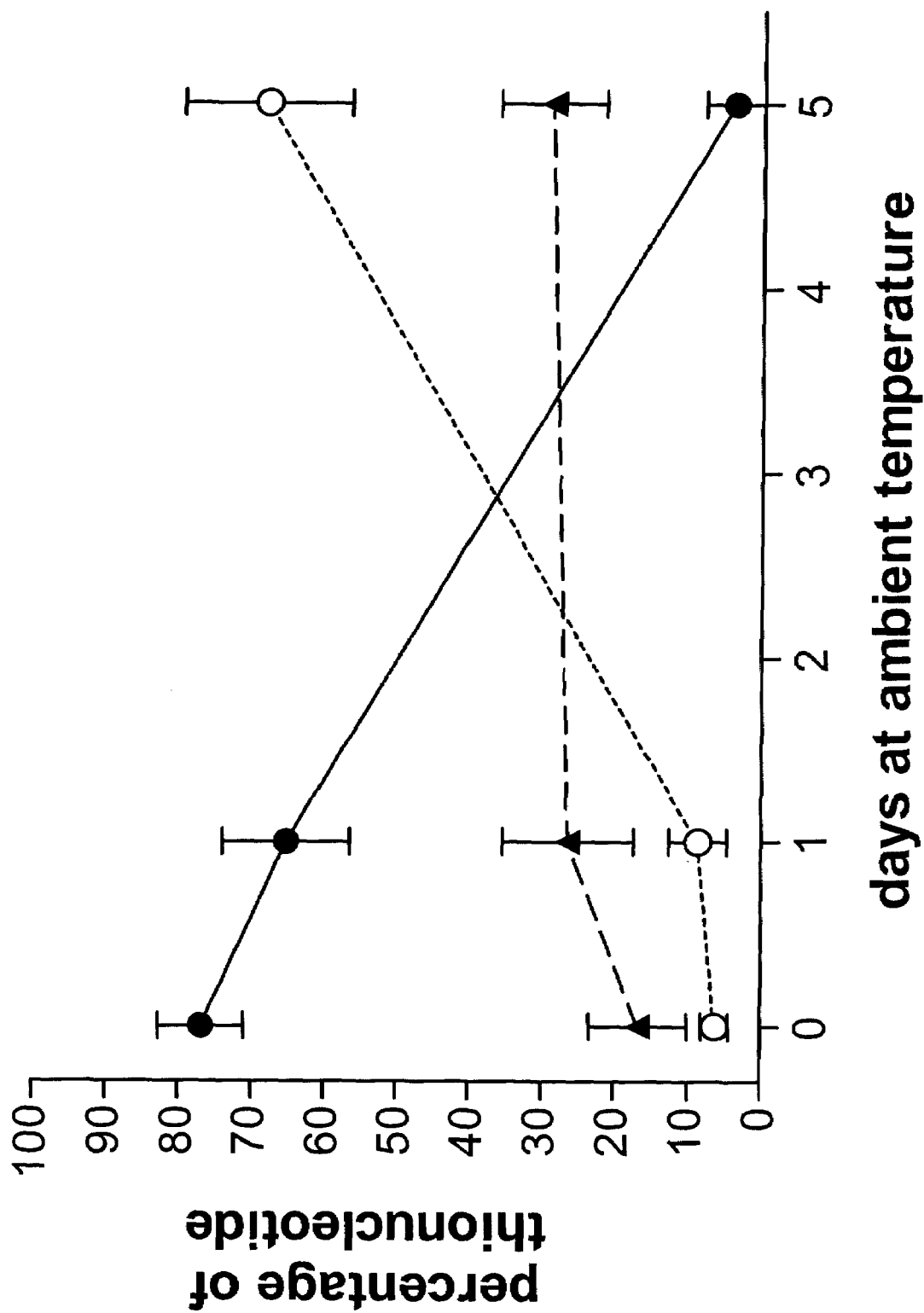
FIG. 10 shows the percentage of 6-thioguanine nucleotides (○ TGMP, ▲ TGDP, ● TGTP) in EDTA blood samples from patients under azathioprine therapy upon storage at ambient temperature (mean±SD, n=3).

In spiked RBC samples containing TGTP or TGDP, a consistent and reproducible interconversion of these metabolites storage at ambient temperature a marked decrease of TGTP was observed (FIG. 10). After 5 days of storage, only about 5% of TGTP could be recovered, while in parallel the amount of TGMP increased considerably to more than 70% of total thioguanosine phosphates. The amount of TGDP did not change significantly.

During storage of RBC from 18 patients at −80° C. for 8 to 14 weeks, the sum of TGTP and TGDP remained unchanged, but the proportion of TGTP decreased by 7.6±7.6%. No difference in decrease was observed whether the samples were stored for 8 or 14 weeks. In these samples, the RBC had been thawed twice. In further experiments, RBC samples which have been repeatedly subjected to thawing and freezing showed progression in dephosphorylation of TGTP to TGDP. These data indicate that the dephosphorylation is influenced more by the thawing process than by storage at −80° C. for this time.

Investigation of the stability of thioguanosine nucleotides in extracted samples revealed a decrease of TGTP proportion of approximately 8% (range from −6 to −13%) upon storage of oxidized samples for 14 days. In a further series, aliquots of the non-oxidized extracts were kept for 14 days at ambient temperature before oxidation. The proportion of TGTP was reduced by 7% on average (range from −5 to −12%) when compared to the first quantification series.

Application to Patient Samples

Figure 11:
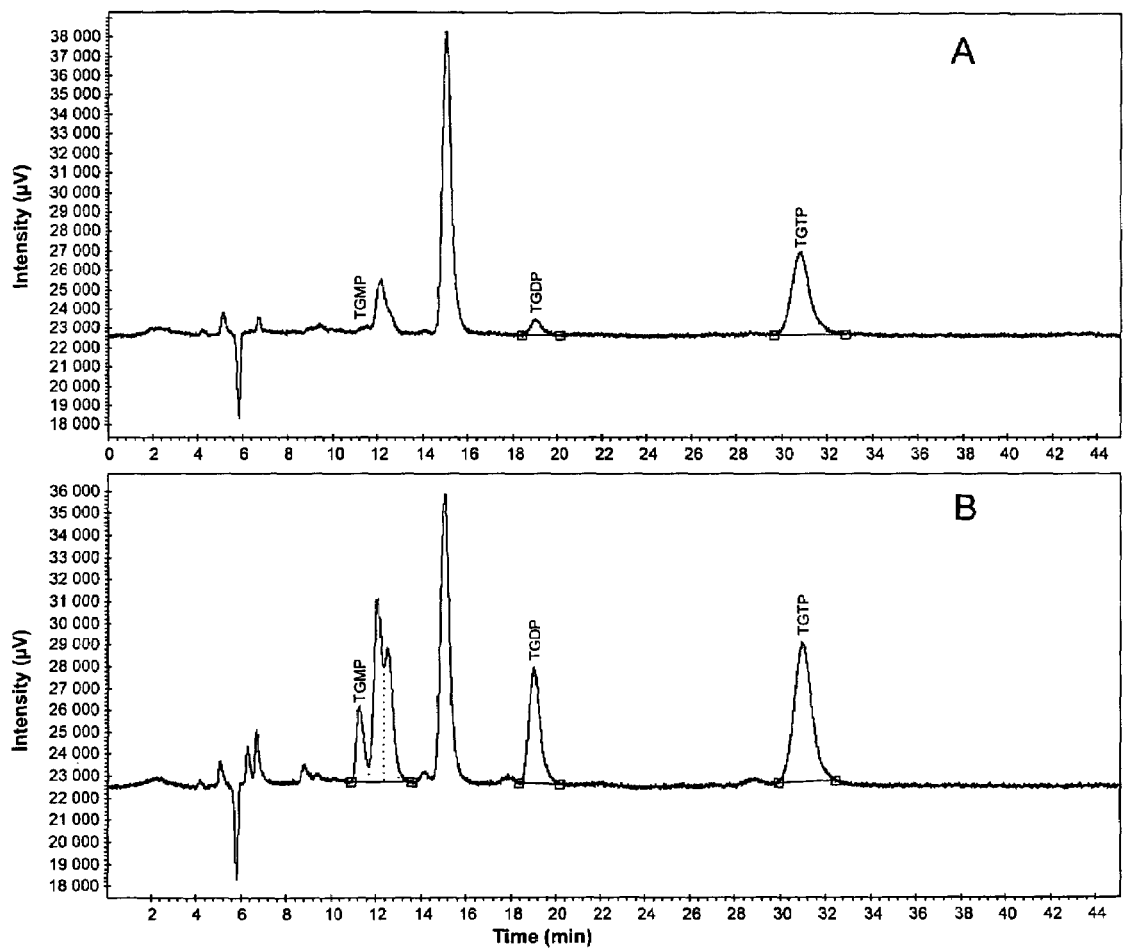
FIG. 11 shows chromatograms of RBC from two patients under azathioprine therapy containing (A) 95 pmol/ml TGDP and 840/ml pmol TGTP or (B) 281 pmol/ml TGMP, 642 pmol/ml TGDP, and 1203 pmol/ml TGTP.

FIG. 11 shows the chromatograms of samples from patients undergoing azathioprine therapy. FIG. 11A exemplifies a chromatogram which is typical for the majority of patients with TGTP as the predominant metabolite accounting for more than 84% of total thioguanine nucleotides, TGDP with approximately 10%, and TGMP with 6%. In contrast, the chromatogram in FIG. 11B shows an exceptional metabolite pattern which was observed in specific patients measured so far in a current study and revealed both TGDP and TGTP to be the major metabolites with 43 and 45% and TGMP with 12%, respectively. The thioguanosine metabolite levels measured in 18 patients are shown in Table 4 and ranged from 494 to 2718 pmol/ml RBC with on average 1259 pmol/ml RBC. Additionally, total thioguanosine nucleotide concentrations were ascertained by an established, independent assay which is applied routinely to determine total 6-TGN levels (Herrlinger et al., Aliment. Pharmacol. Ther. 17:1459-1464 (2003)) and resulted in 1246 pmol/ml on average. The percentage of TGTP in 16 of these patients was similar and ranged from 83.5% to 95.2%, while two patients showed a distinct metabolite pattern with TGTP being 57.2% or 64.3%.

TABLE 4

Determination of thioguanosine phosphates and total 6-TGN levels in patients under azathioprine therapy.

| Patient Number | TGN[a] (pmol/ml RBC) | TGTP + TGDP[b] (pmol/ml RBC) | Percentage of TGTP[c] |
|---|---|---|---|
| 1 | 1579 | 1663 | 92.1 |
| 2 | 838 | 921 | 85.0 |
| 3 | 1370 | 1445 | 91.7 |
| 4 | 1438 | 1223 | 93.5 |
| 5 | 1592 | 1339 | 57.2 |
| 6 | 894 | 774 | 90.7 |
| 7 | 2557 | 1882 | 92.0 |
| 8 | 1322 | 1581 | 64.3 |
| 9 | 657 | 626 | 92.5 |
| 10 | 573 | 520 | 92.3 |
| 11 | 1123 | 1432 | 95.2 |
| 12 | 2530 | 2718 | 83.5 |
| 13 | 450 | 524 | 88.0 |
| 14 | 440 | 494 | 90.9 |
| 15 | 1131 | 1178 | 94.3 |
| 16 | 799 | 860 | 93.5 |
| 17 | 1370 | 1299 | 91.0 |
| 18 | 1763 | 2175 | 92.0 |
| Mean | 1246 | 1259 | 87.7 |

[a] total TGN determined after acid hydrolysis to 6-TG according to Herrlinger et al., supra.
[b] Sum of the individual determined nucleotides.
[c] TGTP × 100/(TGTP + TGDP).

Conclusion:

This example describes a novel method for the rapid, sensitive, and specific determination of the individual 6-thioguanosine-5'-phosphates in RBC of patients undergoing azathioprine therapy. The procedure is based on the lysis of red blood cells followed by extraction and oxidation of the thioguanosine phosphates, which could be separated by ion pair HPLC and quantified by selective and sensitive fluorescence detection. The ease of operation permits performing the assay in routine laboratories. In contrast to the widely used methods for TGN quantification, the present method allows for direct quantification of these active thioguanosine metabolites (i.e., TGMP, TGDP, and TGTP) by a simple procedure that requires less than 0.5 ml aliquots of EDTA blood samples.

Example 3

Measurement of 6-thioguanosine Mono-, Di-, and Triphosphates for Monitoring Azathioprine Therapy in IBD Patients This example illustrates methods for measuring 6-thioguanosine mono- (TGMP), di- (TGDP), and triphosphate (TGTP) levels for monitoring azathioprine therapy in patients with IBD such as CD. Specifically, this example shows that although TGMP levels were only detectable in traces in all patients, TGTP levels could be quantified in all patients and some patients also had significant high levels of TGDP. Further, this example shows that 6-TGN levels have a positive correlation with TGTP concentration. Importantly, this example demonstrates that high TGTP levels and/or high TGTP concentration ratios correlated more closely with clinical outcome than high 6-TGN levels in a subgroup of CD patients. Moreover, this example shows that a subgroup of patients with high levels of TGDP and/or high TGDP concentration ratios (i.e., low TGTP concentration ratios) showed a significantly worse outcome with more flares and a greater demand for anti-TNF treatment.

Methods:

Patients: Patients with CD under long-term azathioprine treatment from the outpatient clinic at the First Department of Medicine of the University of Mainz were included in the present study. The diagnosis of CD was confirmed in all patients by radiographic, endoscopic, and histopathologic parameters. The clinical parameters of the patients are provided in Table 5. Clinical outcomes such as the Crohn's disease activity index (CDAI), number of flares per year, and demand for anti-TNF antibody (e.g., infliximab) treatment were determined on clinical visits.

TABLE 5

Clinical Parameters of CD Patients Included in the Study.

| | |
|---|---|
| Gender (Female:Male) | 48%:52% |
| Age (Years) | 42 (17-78) |
| Mean Duration of Disease (Years) | 15 (0-48) |
| Diseased Area of the Gut | |
| Small and Large Bowel (%) | 59 |
| Large Bowel (%) | 37 |
| Small Bowel (%) | 4 |
| Indication (Refractory Disease:Post Surgery) | 60:40 |
| Average Duration of Therapy (Years) | 3 (0-22) |
| Average Dosage (mg) | 121, 25 (50-300) |

Blood Sampling: Blood samples from patients were collected into EDTA tubes and the packed red blood cells (RBCs) were isolated by centrifugation within 6 hours after blood drawing. The RBCs were immediately frozen at −80° C. until analysis.

TPMT Activity and Quantification of Thioguanosine Nucleotides in RBCs: Thiopurine methyltransferase (TPMT) phenotyping was performed by measuring TPMT enzyme activity in RBCs as described in Kroplin et al., 1998. *Eur. J. Clin. Pharmacol.* 54:265-271 (1998); Schaeffeler et al., *Clin. Chem.* 47:548-555 (2001); and Schaeffeler et al., *Pharmacogenetics* 14:407-417 (2004). TPMT activity<2 nmol 6-MTG×g$^{-1}$ Hb×h$^{-1}$ indicated TPMT deficiency and >23 nmol 6-MTG×g$^{-1}$ Hb×h$^{-1}$ indicated normal TPMT enzyme activity.

6-thioguanine nucleotides (6-TGN) and the methylated metabolites S-methyl-mercaptopurine ribonucleotides (6-MMPR) and S-methyl 6-thioguanosine nucleotides (MTGN) were quantified by a high-performance liquid chromatographic (HPLC) assay as described in Herrlinger et al., *Aliment Pharmacol Ther.* 19:1269-1276 (2004).

The concentrations of 6-thioguanosine 5'-mono-, di-, and triphosphate (TGMP, TGDP, and TGTP, respectively) were determined separately by the method described in Example 2 above. Reference compounds were provided by Jena Bioscience (Jena, Germany). The 5'-phosphates were isolated, extracted, and oxidized as described by Rabel et al., *Anal. Biochem.* 224:315-322 (1995) with slight modifications. HPLC separation was achieved by reversed phase HPLC on a C18 column with phosphate buffer (20 mM, pH 6.8) and 5 mM tetrabutylammonium hydrogen sulfate/acetonitrile 84:16 (v/v) as the mobile phase. Using fluorescence detection, quantification of 6-thioguanosine nucleotides was performed at concentration ranges of 25 to 400 pmol/100 μL RBC for TGTP, 10 to 100 pmol/100 μL for TGDP, and 10 to 50 pmol/100 μL RBC for TGMP.

Statistical analysis: Statistical analysis was based on Wilcoxon tests for inter-individual comparisons of measurement series. Results of these tests were summarized as p-values, where $p<0.05$ indicates local statistical significance.

Results:

A total of 352 consecutive patients from the outpatient clinic of the First Department of Medicine at the University of Mainz were screened for possible inclusion in the present study. 50 patients fulfilled all inclusion criteria and were enrolled in this study, which was conducted between May 2003 and August 2004, while the other 302 were excluded. 3 additional patients had to be excluded from further analysis due to undetectable 6-TGN levels from non-compliance.

Figure 12:
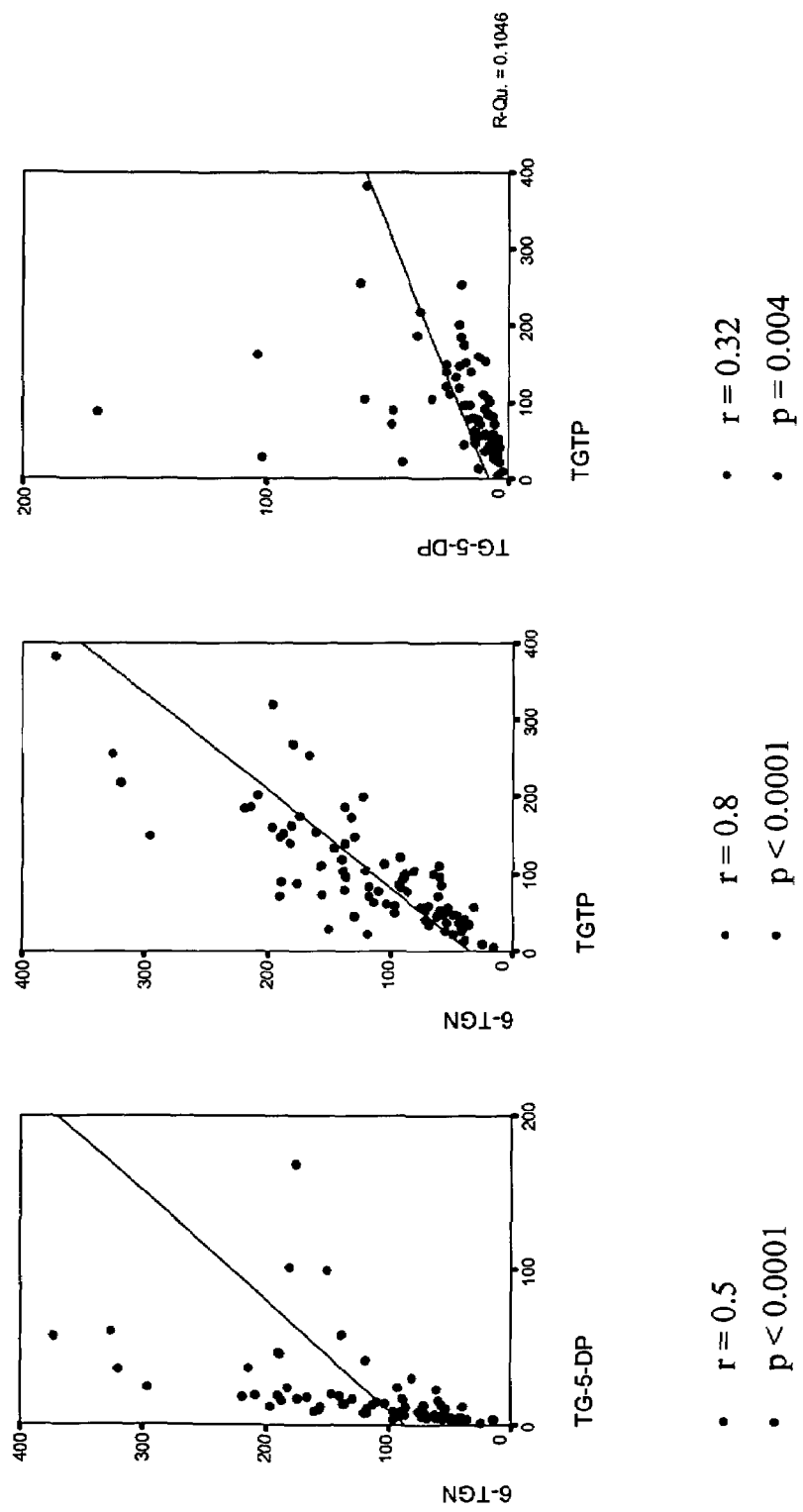
FIG. 12 shows the correlation between 6-TGN, TGTP, and TGDP levels in red blood cells from azathioprine-treated patients with Crohn's disease. Statistically significant correlations are indicated.

6-TGN levels could be determined in all remaining 47 patients. Furthermore, whereas 6-thioguanosine monophosphate (TGMP) levels were only detectable in traces in all patients, 6-thioguanosine triphosphate (TGTP) levels could be quantified in all patients. In addition, a subgroup of the latter patients showed significant high levels of 6-thioguanosine diphosphate (TGDP), whereas another subgroup showed little or no detectable TGDP. 6-TGN levels showed a positive correlation with TGTP ($r=0.8$, $p<0.0001$) and to a lesser extent with TGDP concentrations ($r=0.5$, $p<0.0001$) (FIG. 12). However, little correlation was seen between TGDP and TGTP levels ($r=0.32$, $p<0.004$) (FIG. 12).

Patients were stratified according to their 6-TGN levels and TGTP ratio. The TGTP concentration ratio was calculated as follows: TGTP/(TGTP+TGDP). As shown in Table 6, patients with high 6-TGN levels and a TGTP concentration ratio less than about 0.85 showed worse responses than patients with a ratio greater than about 0.85. The clinical response rate (Response), Crohn's disease activity index (CDAI), number of flares per year (Flares), infliximab use (INF), and the TPMT levels are also shown. Statistically significant differences are indicated by asterisks ($p<0.05$).

Table 6 also shows that at similar TPMT activity values, patients with high 6-TGN levels showed significantly higher response rates (0.42 vs. 0.16) than patients with low 6-TGN levels. However, no significant differences between CDAI levels, number of flares, and demand for infliximab treatment were observed. The subgroup of patients with high 6-TGN and TGDP levels showed a significantly worse clinical outcome with lower response rates (0.15 vs. 0.73), more flares (2.1 vs. 0.2), and higher demand for infliximab treatment (1.1 vs. 0.36) than patients with high 6-TGN and TGTP levels (Table 6).

TABLE 6

Stratification of Patients Based on 6-TGN and TGTP Concentration Ratio.

| n | TGN | TGDP | TGTP | Ratio | Response | CDAI | Flares | INF | TPMT |
|---|---|---|---|---|---|---|---|---|---|
| 26 | 147 ± 7 | 29 ± 7* | 114 ± 10** | 0.81 ± 0.04 | 0.42 ± 0.1* | 206 ± 36 | 1.1 ± 0.6 | 0.7 ± 0.3 | 50 ± 4 |
| 21 | 56 ± 4 | 6 ± 1.1 | 54 ± 6.7 | 0.87 ± 0.024 | 0.16 ± 0.1 | 176 ± 26 | 2.1 ± 0.9 | 1.1 ± 0.5 | 49 ± 1 |
| 13 | 151 ± 14 | 8.7 ± 2.4** | 144 ± 15** | 0.93 ± 0.016 | 0.73 ± 0.1* | 149 ± 35* | 0.2 ± 0.1* | 0.36 ± 0.2 | 46 ± 6 |
| 13 | 147 ± 8 | 52 ± 13 | 87 ± 9 | 0.678 ± 0.055 | 0.15 ± 0.1 | 277 ± 62 | 2.1 ± 0.9 | 1.1 ± 0.5 | 54 ± 4 |
| 15 | 60 ± 4 | 4.6 ± 0.7 | 61 ± 5.7 | 0.919 ± 0.012 | 0.1 ± 0.1 | 189 ± 28 | 1.9 ± 1 | 1.1 ± 0.7 | 48 ± 2 |
| 6 | 46 ± 11* | 9.5 ± 3.4 | 36 ± 18 | 0.748 ± 0.053 | 0.5 ± 0.3 | 151 ± 55 | 1.4 ± 1.3 | 1.0 ± 0.6 | 52 ± 3 |

Discussion:

Using a novel method described in Example 2 to measure individual 6-thioguanosine nucleotides, the present study demonstrates that quantifying TGTP levels and calculating TGTP concentration ratios is useful for monitoring azathioprine therapy or for optimizing clinical responsiveness to azathioprine therapy in patients with inflammatory bowel diseases such as Crohn's disease. The study also indicates that high TGDP levels may be used to predict an inferior response to azathioprine therapy in a subgroup of patients also having high 6-TGN levels.

Previous studies indicated that 6-TGN levels may correlate with clinical outcome in azathioprine or 6-thioguanine treated patients (Dubinsky et al., *Gastroenterol.* 122:904-915 (2002); Dubinsky, *Clin. Gastroenterol. Hepatol.* 2:731-743 (2004)). Although high 6-TGN levels were associated with a significantly higher response rate to azathioprine therapy in the present study, no significant changes between the number of flares and infliximab use were seen. Further, 6-TGN levels correlated with TGTP levels and to a lesser extent with TGDP levels, indicating that TGTP and TGDP levels represent a major proportion of 6-TGN metabolites. However, TGTP and TGDP levels showed little correlation with each other, indicating that the enzymatic conversion from TGDP to TGTP exhibits marked inter-individual differences.

Patients with high 6-TGN levels fell into two subgroups which differed in their TGTP and TGDP levels. The subgroup of patients with high levels of the active metabolite TGTP showed a significantly better outcome with higher response rates, less flares, and lower infliximab use than patients with high 6-TGN and high levels of the precursor metabolite TGDP. In particular, patients with high 6-TGN levels and a low TGTP concentration ratio showed worse responses to azathioprine therapy than patients with high 6-TGN levels and a high TGTP concentration ratio. These findings explain the weak correlation between clinical response to azathioprine therapy and 6-TGN levels. As such, the present study indicates that the active, apoptosis-inducing metabolite TGTP is associated with superior clinical responsiveness to azathioprine therapy, while high levels of TGDP is associated with inferior clinical responsiveness to azathioprine therapy, even in the presence of high 6-TGN levels.

Example 4

Virtual Screening to Identify Candidate Compounds

Virtual Screening. Various software programs such as the UNITY program (Tripos Associates, St. Louis) can be used to screen databases for chemical compounds that are able to fit into the Rac1 surface. The candidate compounds are docked onto the Rac1 surface by using the program FLEXX (Tripos Associates) for energy minimization.

Example 5

Rac1 Inhibition Assay

An assay is used determine compound and metabolite levels using LC/MS/MS, which can be used to quantitatively establish the concentration of the identified compound and the concentrations of its metabolites in an individual's sample. In addition, assays are used to determine Rac1 gene expression, enzyme activity, or protein level in a sample. Gene expression is measured using RT-PCR, and enzyme activity is measured using classical enzyme activity assays, with either detect substrate degradation or product formation. Protein levels are detected using classical immunoassay procedures.

Thereafter, identified compound and/or metabolite levels are measured and gene expression levels, enzyme activity, or protein concentrations can also be simultaneously measured. To determine which compound or metabolite has the most inhibitory effect or therapeutic effect, Rac1 levels are measured in the presence of the compound and/or metabolite by gene expression, enzyme activity, or protein concentration as described above using either cell lines or animal models to determine the most inhibitory molecule of the compound and its metabolites.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A diagnostic method for predicting therapeutic efficacy of azathioprine therapy in an individual, said method comprising:
    (a) providing said individual with azathioprine to induce apoptosis in a cell; and
    (b) determining the concentration of 6-thioguanosine diphosphate (TGDP) and 6-thioguanosine triphosphate (TGTP) in a red blood cell sample from said individual,
    wherein a TGTP concentration greater than 129 pmol/100 µl red blood cells is predictive of superior clinical responsiveness to azathioprine therapy, and
    wherein a TGDP concentration greater than 39 pmol/100 µl red blood cells is predictive of inferior clinical responsiveness to azathioprine therapy.

2. The method of claim 1, wherein said cell of step (a) is an immune cell.

3. The method of claim 2, wherein said immune cell is a T lymphocyte.

4. The method of claim 3, wherein said T lymphocyte is selected from the group consisting of a CD45RA T cell, a CD45RO memory T cell, a CD4-positive T cell, a preactivated T cell, a lamina propria mononuclear cell, and combinations thereof.

5. The method of claim 1, wherein said azathioprine inhibits bcl-$x_L$ mRNA and protein expression.

6. The method of claim 1, wherein said azathioprine inhibits NF-κB p50/p65 activation.

7. The method of claim 1, wherein said azathioprine inhibits IκB phosphorylation.

8. The method of claim 1, wherein said azathioprine inhibits MEK phosphorylation.

9. The method of claim 1, wherein said apoptosis is induced by the binding of said TGTP to Rac 1.

10. The method of claim 1, further comprising increasing a subsequent dose of said azathioprine when said TGDP concentration is greater than 39 pmol/100 µl red blood cells.

11. A method for monitoring azathioprine therapy in an individual, said method comprising measuring the level of 6-thioguanosine diphosphate (TGDP) and 6-thioguanosine triphosphate (TGTP) in a red blood cell sample from said individual,
    wherein a TGTP level greater than 129 pmol/100 µl red blood cells is indicative of superior clinical responsiveness to azathioprine therapy, and
    wherein a TGDP level greater than 39 pmol/100 µl red blood cells is indicative of inferior clinical responsiveness to azathioprine therapy.

12. The method of claim 11 wherein said individual has an inflammatory bowel disease.

13. The method of claim 12, wherein said inflammatory bowel disease is Crohn's disease (CD) or ulcerative colitis (UC).

14. The method of claim 11, wherein said superior clinical responsiveness to azathioprine therapy is associated with a clinical outcome selected from the group consisting of a reduced number of flares, a reduced Crohn's disease activity index (CDAI), a reduced colitis activity index (CAI), a reduced demand for steroid treatment, a reduced demand for anti-TNF antibody treatment, reduced C-reactive protein (CRP) levels, and combinations thereof.

15. The method of claim 11, wherein said superior clinical responsiveness to azathioprine therapy is associated with apoptosis of T lymphocytes.

16. The method of claim 11, wherein said inferior clinical responsiveness to azathioprine therapy is associated with a clinical outcome selected from the group consisting of an increased number of flares, an in creased CDAI, an increased CAI, an increased demand for steroid treatment, an increased demand for anti-TNF antibody treatment, increased CRP levels, and combinations thereof.

17. The method of claim 11, further comprising calculating a concentration ratio using the following formula:

$$\frac{TGTP \text{ level}}{(TGTP \text{ level} + TGDP \text{ level})},$$

wherein a concentration ratio greater than about 0.85 in an individual also having a a 6-thioguanine nucleotide (6-TGN) level greater than 137 pmol/100 μl red blood cells is indicative of superior clinical responsiveness to azathioprine therapy, and wherein a concentration ratio less than about 0.85 in an individual also having a 6-TGN level greater than 137 pmol/100 μl red blood cells is indicative of inferior clinical responsiveness to azathioprine therapy.

18. The method of claim 11, wherein said red blood cell sample is isolated from blood.

19. The method of claim 11, further comprising comparing the level of TGTP and TGDP to the level of TGTP and TGDP measured at an earlier time.

20. A method for monitoring azathioprine therapy in an individual, said method comprising:
(a) measuring the level of 6-thioguanosine diphosphate (TGDP) and 6-thioguanosine triphosphate (TGTP) in a red blood cell sample from said individual; and
(b) calculating a concentration ratio using the following formula:

$$\frac{TGTP \text{ level}}{(TGTP \text{ level} + TGDP \text{ level})},$$

wherein a concentration ratio greater than about 0.85 in an individual also having a 6-thioguanine nucleotide (6-TGN) level greater than 137 pmol/100 μl red blood cells is indicative of superior clinical responsiveness to azathioprine therapy, and wherein a concentration ratio less than about 0.85 in an individual also having a 6-TGN level greater than 137 pmol/100 μl red blood cells is indicative of inferior clinical responsiveness to azathioprine therapy.

21. A method for optimizing clinical responsiveness to azathioprine therapy in an individual, said method comprising:
(a) measuring the level of thioguanosine diphosphate (TGDP) and 6-thioguanosine triphosphate (TGTP) in a red blood cell sample from said individual; and
(b) adjusting the subsequent dose of azathioprine or a metabolite thereof based upon the level of TGDP and TGTP, wherein a TGDP level greater than 22 pmol/100 μl red blood cells is indicative of a need to increase the subsequent dose of said azathioprine or a metabolite thereof.

22. The method of claim 21, wherein said individual has an inflammatory bowel disease.

23. The method of claim 22, wherein said inflammatory bowel disease is Crohn's disease (CD) or ulcerative colitis (UC).

24. The method of claim 21, further comprising calculating a concentration ratio using the following formula:

$$\frac{TGTP \text{ level}}{(TGTP \text{ level} + TGDP \text{ level})},$$

wherein a concentration ratio less than about 0.85 in an individual also having a 6-thioguanine nucleotide (6-TGN) level greater than 137 pmol/100 μl red blood cells is indicative of a need to increase the subsequent dose of said azathioprine or a metabolite thereof.

25. The method of claim 21, wherein said red blood cell sample is isolated from blood.

26. The method of claim 21, further comprising comparing the level of TGTP and TGDP to the level of TGTP and TGDP measured at an earlier time.

27. The method of claim 1, wherein said individual has an inflammatory bowel disease.

28. The method of claim 27, wherein said inflammatory bowel disease is Crohn's disease (CD) or ulcerative colitis (UC).

29. The method of claim 1, wherein said red blood cell sample is isolated from blood.

30. The method of claim 20, wherein said individual has an inflammatory bowel disease.

31. The method of claim 30, wherein said inflammatory bowel disease is Crobn's disease (CD) or ulcerative colitis (UC).

32. The method of claim 20, wherein said red blood cell sample is isolated from blood.

* * * * *

UNITED STATES PATENT AND TRADEMARK OFFICE
CERTIFICATE OF CORRECTION

PATENT NO.            : 7,524,851 B2
APPLICATION NO.       : 11/003306
DATED                 : April 28, 2009
INVENTOR(S)           : Markus F. Neurath and Matthias Schwab It is certified that error appears in the above-identified patent and that said Letters Patent is hereby corrected as shown below:

Claim 21, Column 42, line 14,
"wherein a TGDP level greater than 22 pmol/100 µl red"

Should read,

-- wherein a TGDP level greater than 39 pmol/100 µl red --

Signed and Sealed this
Twenty-second Day of February, 2011

David J. Kappos
*Director of the United States Patent and Trademark Office*